(12) United States Patent
Soon-Shiong

(10) Patent No.: US 12,156,901 B2
(45) Date of Patent: *Dec. 3, 2024

(54) TREATMENT OF IMMUNOSUPPRESSED SUBJECTS

(71) Applicant: NantCell, Inc., Culver City, CA (US)

(72) Inventor: Patrick Soon-Shiong, Culver City, CA (US)

(73) Assignee: NantCell, Inc., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/326,293

(22) Filed: May 31, 2023

(65) Prior Publication Data

US 2023/0330186 A1  Oct. 19, 2023

Related U.S. Application Data

(63) Continuation of application No. 17/284,406, filed as application No. PCT/US2019/055790 on Oct. 11, 2019, now Pat. No. 11,701,408.

(60) Provisional application No. 62/744,601, filed on Oct. 11, 2018.

(51) Int. Cl.
| | | |
|---|---|---|
| *A61K 38/20* | (2006.01) | |
| *A61K 31/427* | (2006.01) | |
| *A61K 31/4418* | (2006.01) | |
| *A61K 31/496* | (2006.01) | |
| *A61K 31/513* | (2006.01) | |
| *A61K 31/52* | (2006.01) | |
| *A61K 31/536* | (2006.01) | |
| *A61K 31/635* | (2006.01) | |
| *A61K 31/675* | (2006.01) | |
| *A61K 31/7068* | (2006.01) | |
| *A61K 31/7072* | (2006.01) | |
| *A61K 38/17* | (2006.01) | |
| *A61K 47/64* | (2017.01) | |
| *A61P 31/18* | (2006.01) | |

(52) U.S. Cl.
CPC ........ *A61K 38/2086* (2013.01); *A61K 31/427* (2013.01); *A61K 31/4418* (2013.01); *A61K 31/496* (2013.01); *A61K 31/513* (2013.01); *A61K 31/52* (2013.01); *A61K 31/536* (2013.01); *A61K 31/635* (2013.01); *A61K 31/675* (2013.01); *A61K 31/7068* (2013.01); *A61K 31/7072* (2013.01); *A61K 38/1793* (2013.01); *A61K 47/642* (2017.08); *A61K 47/6425* (2017.08); *A61P 31/18* (2018.01)

(58) Field of Classification Search
CPC ............ A61K 38/2086; A61K 47/6425; A61K 47/642; A61K 31/427; A61K 31/4418; A61K 31/496; A61K 31/513; A61K 31/52; A61K 31/536; A61K 31/635; A61K 31/675; A61K 31/7068; A61K 31/7072; A61K 38/1793; A61P 31/18

See application file for complete search history.

(56) References Cited

U.S. PATENT DOCUMENTS

| | | | |
|---|---|---|---|
| 8,242,106 B2 * | 8/2012 | Howbert | C08B 37/0012 540/593 |
| 9,255,141 B2 | 2/2016 | Wong et al. | |
| 9,925,247 B2 | 3/2018 | Liu et al. | |
| 2006/0106043 A1 * | 5/2006 | Kraft | A61K 45/06 514/269 |
| 2011/0081311 A1 | 4/2011 | Pavlakis | |
| 2015/0374790 A1 * | 12/2015 | Liu | A61P 35/00 424/85.2 |
| 2021/0379156 A1 | 12/2021 | Soon-Shiong | |

FOREIGN PATENT DOCUMENTS

| | | |
|---|---|---|
| WO | WO 2016/004060 | 1/2016 |
| WO | WO 2017/0177175 | 10/2017 |
| WO | WO 2019/245993 | 12/2019 |

OTHER PUBLICATIONS

Definition of adoptive cell transfer NCI Dictionary of Cancer Terms—NCI.pdf (Year: 2022).
Davis et al., "A Phase 1 Study of ALT-803 (IL-15 superagonist) to Clear Latent HIV Reservois," Poster #356, Croiconference 2018, www.croiconference.org/sites/default/files/posters-2018/1430_Davis_356.pdf.
Ellis-Connell et al., "ALT-803 Transiently Reduces Simian Immunodeficiency Virus Replication in the Absence of Antiretroviral Treatment," Journal of Virology, Feb. 2018, vol. 92(3), pp. 1-21.
Romee et al., First-in-human phase 1 clinical study of the IL-15 superagonist complex ALT-803 to treat relapse after transplantation, Blood, Jun. 2018, vol. 131(23), pp. 2515-2527.
Webb et al., "The human IL-15 superagonist ALT-803 directs SIV-specific CD81 T cells into B-cell follicles," Blood Advances, Jan. 23, 2018, vol. 2(2), pp. 76-84.
International Search Report and Written Opinion for International (PCT) Patent Application No. PCT/US2019/055790, dated Mar. 12, 2020 13 pages.

(Continued)

*Primary Examiner* — Michael P Cohen

(74) *Attorney, Agent, or Firm* — Sheridan Ross P.C.

(57) ABSTRACT

An IL-15 super agonist (IL-15N72D:IL-15RαSU/IgG1Fc; N-803) increases circulating NK cells, effector memory and effector memory RA cells in post-allogeneic hematopoietic stem cell transplant patients (HCT). Methods of treatment include administration of N-803 to subjects in need of such treatment.

15 Claims, 10 Drawing Sheets

Specification includes a Sequence Listing.

(56) References Cited

OTHER PUBLICATIONS

International Preliminary Report on Patentability for International (PCT) Patent Application No. PCT/US2019/055790, dated Apr. 22, 2021 9 pages.
Official Action for U.S. Appl. No. 17/284,406 dated Jul. 29, 2022 21 pages.
Final Action for U.S. Appl. No. 17/284,406 dated Nov. 17, 2022 16 pages.
Notice of Allowance for U.S. Appl. No. 17/284,406 dated Mar. 1, 2023 7 pages.

* cited by examiner

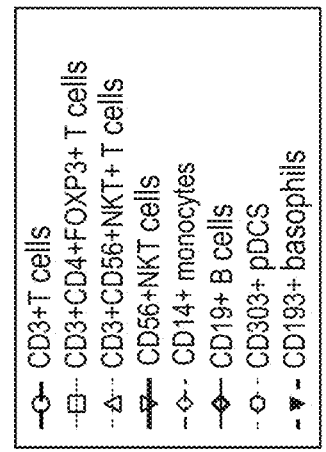
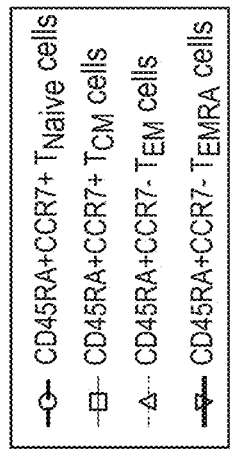
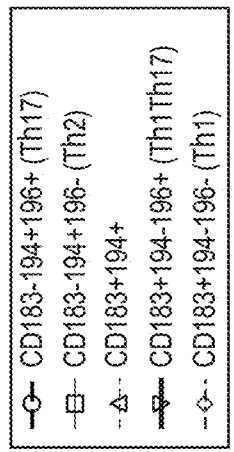
FIG. 2A
FIG. 2B
FIG. 2C
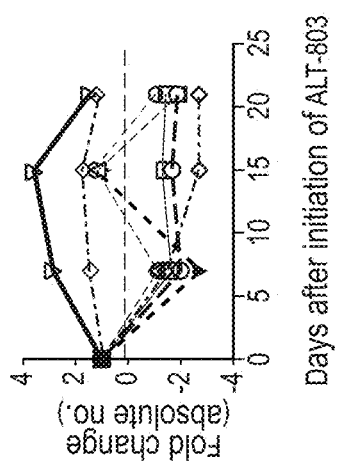
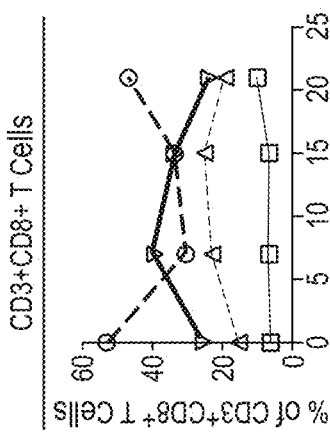
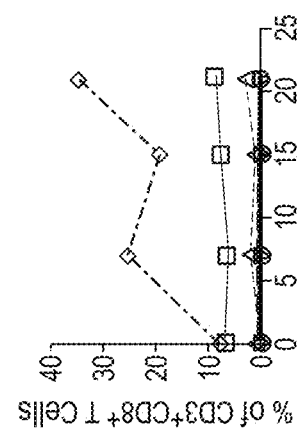

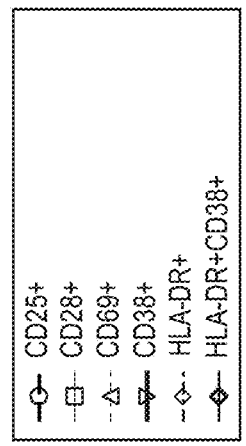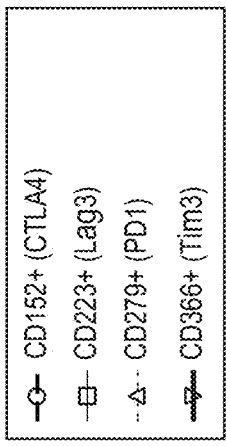
FIG. 2D
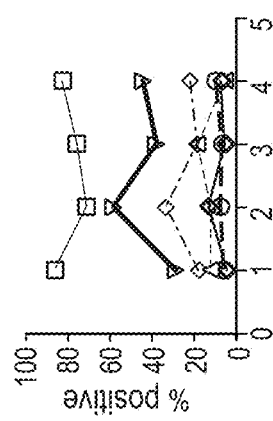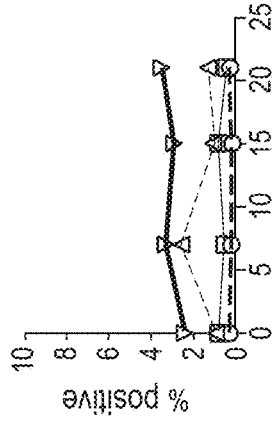
FIG. 2E
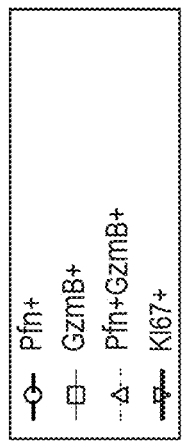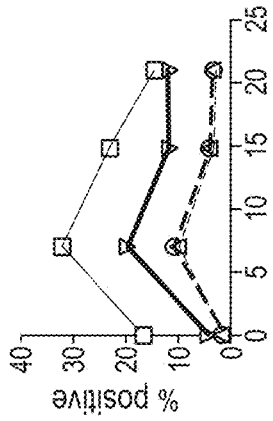
FIG. 2F
Days after initiation of ALT-803

Demographic Characteristics

N=16

| Avg Age (yrs) | Avg Entry CD4 | Avg Yrs HIV+ | Avg Yrs on ART |
|---|---|---|---|
| 43 | 821 | 12 | 9 |

FIG. 4

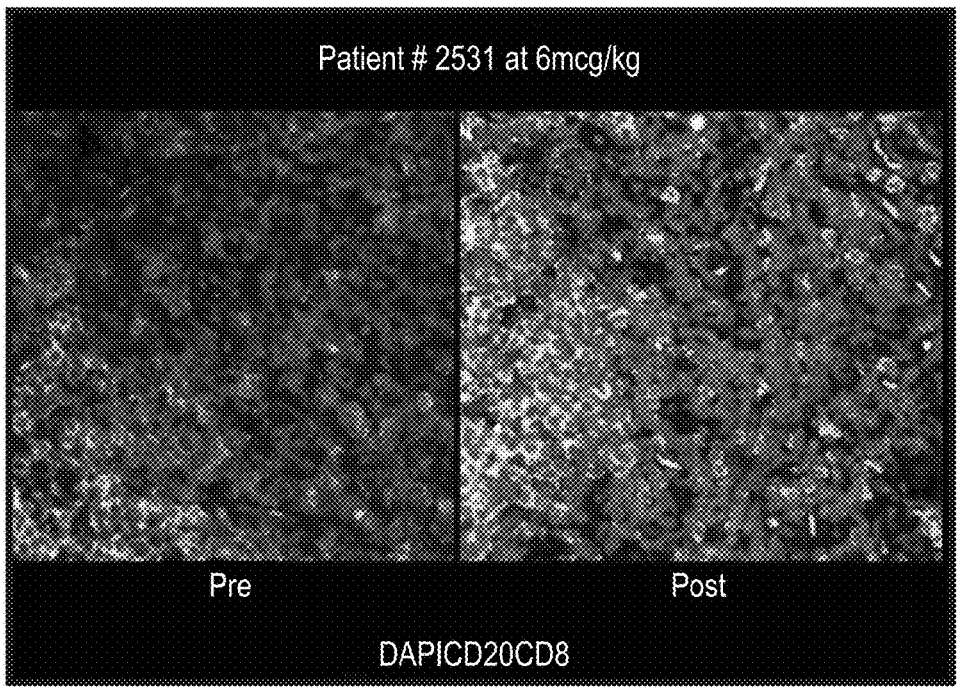

FIG. 9

N-803 Increases Homing of NK Cells to Lymph Node
Before N-803

Administration of N-803 results in accumulation of NK cells in lymph nodes latently infected cells reside CD56 Staining of LN before (A) and 1 week after (B) the 3rd dose of N-803 in participant 2543 (3.0 mcg/kg SC)

FIG. 10A

N-803 Increases Homing of NK Cells to Lymph Node
After N-803

CD56 Staining of LN before (A) and 1 week after (B) the 3rd dose of N-803 in participant 2543 (3.0 mcg/kg SC)

FIG. 10B

SEQUENCE LISTING

```
Sequence total quantity: 6
SEQ ID NO: 1            moltype = DNA  length = 405
FEATURE                 Location/Qualifiers
source                  1..405
                        mol_type = other DNA
                        organism = synthetic construct
SEQUENCE: 1
atggagacag acacactcct gttatgggta ctgctgctct gggttccagg ttccaccggt  60
aactgggtga atgtaataag tgatttgaaa aaaattgaag atcttattca atctatgcat  120
attgatgcta ctttatatac ggaaagtgat gttcacccca gttgcaaagt aacagcaatg  180
aagtgctttc tcttggagtt acaagttatt tcacttgagt ccggagatgc aagtattcat  240
gatacagtag aaaatctgat catcctagca aacgacagtt tgtcttctaa tgggaatgta  300
acagaatctg gatgcaaaga atgtgaggaa ctggaggaaa aaaatattaa agaatttttg  360
cagagttttg tacatattgt ccaaatgttc atcaacactt cttaa             405

SEQ ID NO: 2            moltype = AA  length = 134
FEATURE                 Location/Qualifiers
source                  1..134
                        mol_type = protein
                        organism = synthetic construct
SEQUENCE: 2
METDTLLLWV LLLWVPGSTG NWVNVISDLK KIEDLIQSMH IDATLYTESD VHPSCKVTAM  60
KCFLLELQVI SLESGDASIH DTVENLIILA NDSLSSNGNV TESGCKECEE LEEKNIKEFL  120
QSFVHIVQMF INTS                                                    134

SEQ ID NO: 3            moltype = AA  length = 114
FEATURE                 Location/Qualifiers
source                  1..114
                        mol_type = protein
                        organism = synthetic construct
SEQUENCE: 3
NWVNVISDLK KIEDLIQSMH IDATLYTESD VHPSCKVTAM KCFLLELQVI SLESGDASIH  60
DTVENLIILA NDSLSSNGNV TESGCKECEE LEEKNIKEFL QSFVHIVQMF INTS        114

SEQ ID NO: 4            moltype = DNA  length = 951
FEATURE                 Location/Qualifiers
source                  1..951
                        mol_type = other DNA
                        organism = synthetic construct
SEQUENCE: 4
atggacagac ttacttcttc attcctgctc ctgattgtcc ctgcgtacgt cttgtccatc  60
acgtgccctc cccccatgtc cgtggaacac gcagacatct gggtcaagag ctacagcttg  120
tactccaggg agcggtacat ttgtaactct ggtttcaagc gtaaagccgg cacgtccagc  180
ctgacggagt gcgtgttgaa caaggccacg aatgtcgccc actggacaac ccccagtctc  240
aaatgtatta gagagcccaa atcttgtgac aaaactcaca catgcccacc gtgcccagca  300
cctgaactcc tggggggacc gtcagtcttc ctcttccccc caaaacccaa ggacaccctc  360
atgatctccc ggacccctga ggtcacatgc gtggtggtgg acgtgagcca cgaagaccct  420
gaggtcaagt tcaactggta cgtggacggc gtggaggtgc ataatgccaa gacaaagccg  480
cgggaggagc agtacaacag cacgtaccgt gtggtcagcg tcctcaccgt cctgcaccag  540
```

```
                                                                -continued
gactggctga  atggcaagga  gtacaagtgc  aaggtctcca  acaaagcoct  cccagccccc   600
atcgagaaaa  ccatctccaa  agccaaaggg  cagccccgag  aaccacaggt  gtacaccctg   660
cccccatccc  gggatgagct  gaccaagaac  caggtcagcc  tgacctgcct  ggtcaaaggc   720
ttctatccca  gcgacatcgc  cgtggagtgg  gagagcaatg  ggcagccgga  gaacaactac   780
aagaccacgc  ctcccgtgct  ggactccgac  ggctccttct  tcctctacag  caagctcacc   840
gtggacaaga  gcaggtggca  gcaggggaac  gtcttctcat  gctccgtgat  gcatgaggct   900
ctgcacaacc  actacacgca  gaagagcctc  tccctgtctc  cgggtaaata  a            951

SEQ ID NO: 5            moltype = AA  length = 316
FEATURE                 Location/Qualifiers
source                  1..316
                        mol_type = protein
                        organism = synthetic construct
SEQUENCE: 5
MDRLTSSFLL  LIVPAYVLSI  TCPPPMSVEH  ADIWVKSYSL  YSRERYICNS  GFKRKAGTSS   60
LTECVLNKAT  NVAHWTTPSL  KCIREPKSCD  KTHTCPPCPA  PELLGGPSVF  LFPPKPKDTL   120
MISRTPEVTC  VVVDVSHEDP  EVKFNWYVDG  VEVHNAKTKP  REEQYNSTYR  VVSVLTVLHQ   180
DWLNGKEYKC  KVSNKALPAP  IEKTISKAKG  QPREPQVYTL  PPSRDELTKN  QVSLTCLVKG   240
FYPSDIAVEW  ESNGQPENNY  KTTPPVLDSD  GSFFLYSKLT  VDKSRWQQGN  VFSCSVMHEA   300
LHNHYTQKSL  SLSPGK                                                      316

SEQ ID NO: 6            moltype = AA  length = 297
FEATURE                 Location/Qualifiers
source                  1..297
                        mol_type = protein
                        organism = synthetic construct
SEQUENCE: 6
ITCPPPMSVE  HADIWVKSYS  LYSRERYICN  SGFKRKAGTS  SLTECVLNKA  TNVAHWTTPS   60
LKCIREPKSC  DKTHTCPPCP  APELLGGPSV  FLFPPKPKDT  LMISRTPEVT  CVVVDVSHED   120
PEVKFNWYVD  GVEVHNAKTK  PREEQYNSTY  RVVSVLTVLH  QDWLNGKEYK  CKVSNKALPA   180
PIEKTISKAK  GQPREPQVYT  LPPSRDELTK  NQVSLTCLVK  GFYPSDIAVE  WESNGQPENN   240
YKTTPPVLDS  DGSFFLYSKL  TVDKSRWQQG  NVFSCSVMHE  ALHNHYTQKS  LSLSPGK      297
```

TREATMENT OF IMMUNOSUPPRESSED SUBJECTS

CROSS-REFERENCE TO RELATED APPLICATIONS

This application is a continuation application of U.S. patent application Ser. No. 17/284,406, filed Apr. 9, 2021, now U.S. Pat. No. 11,701,408, which is a national stage under 35 U.S.C. 371 and claims the benefit of PCT Application No. PCT/US2019/55790 having an international filing date of Oct. 11, 2019, which designates the United States, which PCT claims the benefit of priority under 35 U.S.C. § 119(e) to U.S. Provisional Application No. 62/744,601, filed on Oct. 11, 2018. The entire contents of each of the foregoing applications are hereby incorporated by reference in their entireties.

REFERENCE TO SEQUENCE LISTING

This application contains a Sequence Listing submitted as an electronic XML file named "PAT 001418_US003.xml", having a size in of 9000 bytes, and created on May 31, 2023. The information contained in this XML file is hereby incorporated by reference in its entirety pursuant to 37 CFR § 1.52(e)(5).

FIELD OF THE INVENTION

Embodiments of the invention are directed to compositions for treating immunosuppressed patients, patients with neoplasia or virus infections. In particular, the compositions include a superagonist.

BACKGROUND

Immunosuppression is a reduction of the activation or efficacy of the immune system. Some portions of the immune system itself have immunosuppressive effects on other parts of the immune system, and immunosuppression may occur as an adverse reaction to treatment of other conditions.

In general, immunosuppression is the deliberate prevention or reduction of an immune response. It can result from the administration of immunosuppressive agents or from the deliberate depletion of immune cells, as well as from malnutrition, cancers and certain chronic infections such as HIV. Deliberately induced immunosuppression is performed to prevent the body from rejecting an organ transplant. Additionally deliberate immunosuppression is used for treating graft-versus-host disease after a bone marrow transplant, or for the treatment of auto-immune diseases such as systemic lupus erythematosus, rheumatoid arthritis, Sjögren's syndrome, or Crohn's disease. This is typically done using medications, but may involve surgery (splenectomy), plasmapheresis, or radiation. An unwanted side-effect of immunosuppression is immunodeficiency.

SUMMARY

Embodiments of the invention are directed, in part, to compositions which modulate immune cell responses, for example, immunosuppressed subjects such as those having undergone post-allogeneic hematopoietic stem cell transplant (HCT), patients with neoplasia or virus infections. Methods of treatment include administration of compositions comprising therapeutically effective amounts of an IL-15:IL-15Rα complex.

In certain embodiments, a method of treating a subject suffering from a human immunodeficiency virus (HIV) infection comprises administering to the subject a composition comprising a therapeutically effective amount of an IL-15:IL-15Rα (N-803) complex, wherein the IL-15:IL-15Rα complex modulates amounts of circulating immune effector cells and/or activates immune effector cells. In embodiments, the IL-15:IL-15Rα complex is an IL-15N72D:IL-15RαSu/Fc complex (N-803) comprising a dimeric IL-15RαSu/Fc and two IL-15N72D molecules. The HIV infection is active or in a latent stage.

In certain embodiments, the IL-15:IL-15Rα complex is administered to the subject in escalating therapeutically effective amounts over a period of time to maintain an HIV specific immune response. In certain aspects the dose is escalated to a maximum therapeutically effective amount which is not toxic to the subject as determined by a dose-limiting toxicity (DLT) assay. In certain embodiments, the IL-15:IL-15Rα complex is administered until the HIV is undetectable or eradicated from the subject. In certain embodiments, the therapeutically effective amount of the IL-15:IL-15Rα complex is from about 0.01 mcg/kg to about 100.0 mcg/kg. In certain embodiments, the therapeutically effective amount is from about 1 mcg/kg to about 6.0 mcg/kg. In certain embodiments, the routes of administration of the IL-15:IL-15Rα complex to the subject comprise: subcutaneous, intravenous, intraperitoneal, intramuscular, intratumoral or intradermal routes. In certain embodiments, the immune effector cells comprise natural killer cells (NK), cytolytic $CD8^+$ T cells (CTLs), $CD4^+$ T helper cells ($T_H$), effector memory ($T_{EM}$) T cells ($CD45RA^-/CCR7^-$), effector memory RA ($T_{EMRA}$) T cells ($CD45RA^-/CCR7^-$), or combinations thereof.

In certain embodiments, a subject is treated with the IL-15:IL-15Rα complex in combination with one or more therapeutics comprising one or more chemotherapeutic agents, compounds, cytokine antagonists, cytokine receptor antagonists, cytokines, adoptive cell therapy, anti-viral agents, checkpoint inhibitors, adjuvants or combinations thereof. In the anti-viral agent comprises a non-nucleoside reverse transcriptase inhibitor (NNRTI), a nucleoside reverse transcriptase inhibitor (NRTI), a protease inhibitor or combinations thereof. In certain embodiments, the NNRTI comprises: etravirine, efavirenz, nevirapine, rilpivirine, delavirdine, nevirapine or combinations thereof. In certain embodiments, the NRTI comprises: lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate or combinations thereof. In certain embodiments, the protease inhibitor comprises: amprenavir, tipranavir, indinavir, saquinavir mesylate, lopinavir and ritonavir (LPV/RTV), Fosamprenavir Calcium (FOS-APV), ritonavir, darunavir, atazanavir sulfate, nelfinavir mesylate or combinations thereof.

In certain embodiments, the treatment with IL-15:IL-15Rα is combined with adoptive cell therapy. In certain embodiments, the method comprises culturing cells ex vivo with an effective amount of IL-15:IL-15Rα complex and adoptively transferring the cells to the subject. In certain embodiments, the cells comprise immune effector cells, stem cells or combinations thereof. In certain embodiments, the adoptively transferred cells comprise: allogeneic, autologous, syngeneic, related, unrelated, HLA-matched, HLA-mismatched or haploidentical cells.

In certain embodiments, a method of treating immunosuppressed subjects, comprises administering to the subject a composition comprising a therapeutically effective amount of an IL-15:IL-15Rα complex, wherein the IL-15:IL-15Rα complex increases the number of circulating immune effector cells, immune cell activity and/or activates immune effector cells, thereby upregulating immunity in the immunosuppressed subject. In certain aspects, the IL-15:IL-15Rα complex is an IL-15N72D:IL-15RαSu/Fc complex (N-803) comprising a dimeric IL-15RαSu/Fc and two IL-15N72D molecules. In certain aspects, the immune effector cells comprise natural killer cells (NK), effector memory ($T_{EM}$), effector memory RA ($T_{EMRA}$) T cells, cytolytic T cells (CTLs), T helper cells ($T_H$) or combinations thereof. These immune cells are identified by various markers comprising CXCR3, effector memory $T_{EM}$ markers CD45RA$^-$/CCR7$^-$ or $T_{EMRA}$ markers CD45RA$^-$/CCR7$^-$. In certain embodiments, activated immune effector cells comprise one or more markers comprising CD38, perforin, granzyme B, Ki-67 or combinations thereof.

In certain embodiments, the immunosuppressed subjects comprise subjects having undergone organ transplantation, bone marrow transplantation, radiotherapy, chemotherapy and/or have a virus infection, chronic virus infection, recurrent virus infection, or combinations thereof.

In certain embodiments it may be preferable to administer to a subject, one or more other agents which are of therapeutic benefit. These include without limitation, chemotherapeutic agents, compounds, cytokine antagonist, cytokine receptor antagonist, cytokines, adoptive cell therapy, anti-viral agents, checkpoint inhibitors, adjuvants or combinations thereof. In certain embodiments, compounds comprise at least one amidoamine compound. Amidoamines are a class of chemical compounds that are formed from fatty acids and diamines. An example of an amidoamine compound is myristamidopropyl dimethylamine (Aldox).

In certain embodiments, a method of preventing or treating a virus infection comprises administering to the subject a composition comprising a therapeutically effective amount of an IL-15:IL-15Rα complex, wherein the IL-15:IL-15Rα complex increases the number of circulating immune effector cells and/or activates immune effector cells. In certain aspects, the immune effector cells comprise natural killer cells (NK), effector memory ($T_{EM}$), effector memory RA ($T_{EMRA}$) T cells, cytolytic T cells (CTLs), T helper cells ($T_H$) or combinations thereof. These immune cells are identified by various markers comprising CXCR3, effector memory $T_{EM}$ markers CD45RA$^-$/CCR7$^-$ or $T_{EMRA}$ markers CD45RA$^-$/CCR7$^-$. In certain embodiments, activated immune effector cells comprise one or more markers comprising CD38, perforin, granzyme B, Ki-67 or combinations thereof.

In certain embodiments, the subject to be treated will not be suffering from cancer. In additional embodiments, the subject will not be suffering from a viral infection such as HCV, HIV, etc. In yet additional embodiments, the subject will not be suffering from a bacterial infection (e.g., gram positive or gram negative bacteria).

In certain embodiments, the treatment approaches of the invention could also be combined with any of the following therapies: radiation, chemotherapy, surgery, therapeutic antibodies, immunomodulatory agents, proteasome inhibitors, pan-DAC inhibitors, H-DAC inhibitors, checkpoint inhibitors, adoptive cell therapies include CAR T and NK cell therapy and vaccines.

Exemplary effective doses of the IL-15:IL-15Rα complex (N-803) include between 0.1 µg/kg and 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 µg/kg body weight or 1, 2, 3, 4, 5, 6, 7, 8, 9, 10, 20, 30, 40, 50, 60, 70, 80, 90, or 100 mg/kg body weight.

In some cases, the N-803 is administered daily, e.g., every 24 hours. Or, the N-803 is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours.

Exemplary effective daily doses of N-803 include between 0.1 µg/kg and 100 µg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 µg/kg body weight.

Alternatively, the N-803 is administered about once per week, e.g., about once every 7 days. Or, the N-803 is administered twice per week, three times per week, four times per week, five times per week, six times per week, or seven times per week. Exemplary effective weekly doses of N-803 include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. For example, an effective weekly dose of N-803 is between 0.1 µg/kg body weight and 400 µg/kg body weight. Alternatively, N-803 is administered at a fixed dose or based on body surface area (i.e., per m$^2$).

In some cases, subjects receive two 6-week cycles consisting of 4 weekly N-803 intravenous doses followed by a 2-week rest period. Ultimately, the attending physician or veterinarian decides the appropriate amount and dosage regimen.

In certain embodiments, the compositions described herein are administered systemically, intravenously, subcutaneously, intramuscularly, intraperitoneally, intravesically, or by instillation. The antibody and N-803 may be administered simultaneously or sequentially.

In other embodiments, treatment of immunosuppressed subjects with N-803 increases circulating immune cell numbers and/or activity by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% as compared to a baseline control.

In another embodiment, treatment of subjects having a neoplasia or virus infection with N-803 results in anti-neoplastic or anti-viral immune effector cell killing of neoplastic cells or virus-infected cells by at least 5% greater, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% greater than that seen with subjects that were not treated with N-803.

In preferred embodiments, tumor-specific effector cells in the subject are augmented by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following the N-803 administration.

In preferred embodiments, virus-specific effector cells in the subject are augmented by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% following the N-803 administration.

The subject is preferably a mammal in need of such treatment, e.g., a subject that has been diagnosed with a neoplasia or a predisposition thereto. The mammal is any mammal, e.g., a human, a primate, a mouse, a rat, a dog, a cat, a horse, as well as livestock or animals grown for food consumption, e.g., cattle, sheep, pigs, chickens, and goats. In a preferred embodiment, the mammal is a human.

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant a peptide, nucleic acid molecule, small compound, nucleic acid based moiety, antibody, antibody-based molecule, protein, protein-based molecule and/or substance for use in the prevention, treatment, management and/or diagnosis of cancer. An exemplary therapeutic agent is N-803. By "N-803" is meant a complex comprising IL-15N72D noncovalently associated with a dimeric IL-15RαSu/Fc fusion protein and having immune stimulating activity. In one embodiment, the IL-15N72D and/or IL-15RαSu/Fc fusion protein comprises one, two, three, four or more amino acid variations relative to a reference sequence. An exemplary IL-15N72D amino acid sequence is provided below.

By "ameliorate" is meant decrease, suppress, attenuate, diminish, arrest, or stabilize the development or progression of a disease.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

The term "antibody" or "immunoglobulin" is intended to encompass both polyclonal and monoclonal antibodies. The preferred antibody is a monoclonal antibody reactive with the antigen. The term "antibody" is also intended to encompass mixtures of more than one antibody reactive with the antigen (e.g., a cocktail of different types of monoclonal antibodies reactive with the antigen). The term "antibody" is further intended to encompass whole antibodies, biologically functional fragments thereof, single-chain antibodies, and genetically altered antibodies such as chimeric antibodies comprising portions from more than one species, bifunctional antibodies, antibody conjugates, humanized and human antibodies. Biologically functional antibody fragments, which can also be used, are those peptide fragments derived from an antibody that are sufficient for binding to the antigen. "Antibody" as used herein is meant to include the entire antibody as well as any antibody fragments (e.g. F(ab')2, Fab', Fab, Fv) capable of binding the epitope, antigen or antigenic fragment of interest. By "binding to" a molecule is meant having a physicochemical affinity for that molecule.

The term "anti-viral agent" or "anti-retroviral agent" as used herein, refers to any molecule that is used for the treatment of a virus and include agents which alleviate any symptoms associated with the virus, for example, antipyretic agents, anti-inflammatory agents, chemotherapeutic agents, and the like. An antiviral agent includes, without limitation: antibodies, aptamers, adjuvants, anti-sense oligonucleotides, chemokines, cytokines, immune stimulating agents, immune modulating agents, B-cell modulators, T-cell modulators, NK cell modulators, antigen presenting cell modulators, enzymes, siRNA's, ribavirin, protease inhibitors, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, or combinations thereof. The term also refers to non-nucleoside reverse transcriptase inhibitors (NNRTIs), nucleoside reverse transcriptase inhibitors (NRTIs), analogs, variants etc.

By "cancer" as used herein is meant, a disease, condition, trait, genotype or phenotype characterized by unregulated cell growth or replication as is known in the art; including colorectal cancer, as well as, for example, leukemia, e.g., acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkin's lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of its environment, alone or in combination with other therapies.

By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

As used herein, the term "cancer therapy" refers to a therapy useful in treating cancer. Examples of anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN™), anti-CD20 antibodies, an epidermal growth factor receptor (EGFR) antagonist (e.g., a tyrosine kinase inhibitor), HER1/EGFR inhibitor (e.g., erlotinib (TARCEVA™)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

A "chemotherapeutic agent" is a chemical compound useful in the treatment of cancer. Examples of chemotherapeutic agents include Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolmelamine; acetogenins (especially bullatacin and bullatacinone); a camptothecin (including the synthetic analogue topotecan); bryostatin; callystatin; CC-1065 (including its adozcicsin, carzicsin and bizicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin omega 1 (*Angew Chem. Intl. Ed. Engl.* (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxy-doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, strcptonigrin, streptozocin, tubcrcidin, ubenimcx, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosinc; arabinoside ("Ara-C"); cyclophosphamidc; thiotcpa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™ (tamoxifen)), raloxifene, droloxifene, 4-hydroxytamoxifen, trioxifene, keoxifene, LY117018, onapristone, and FARESTON™ (toremifene); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane), formestanie, fadrozole, RIVISOR™ (vorozole), FEMARAT™ (letrozole), and ARIMIDEX™ (anastrozole); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii)

ribozymes such as a VEGF expression inhibitor (e.g., ANGIOZYME™ (ribozyme)) and a HER2 expression inhibitor; (ix) vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIX™ rmRH; (x) anti-angiogenic agents such as bevacizumab (AVASTIN™, Genentech); and (xi) pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE™, Rhone-Poulenc Rorer), derived from the European yew, is a semisynthetic analogue of paclitaxel (TAXOL™, Bristol-Myers Squibb). Paclitaxel and docetaxel promote the assembly of microtubules from tubulin dimers and stabilize microtubules by preventing depolymerization, which results in the inhibition of mitosis in cells.

By the terms "effective amount" and "therapeutically effective amount" of a formulation or formulation component is meant a sufficient amount of the formulation or component, alone or in a combination, to provide the desired effect. For example, by "an effective amount" is meant an amount of a compound, alone or in a combination, required to ameliorate the symptoms of a disease relative to an untreated patient. The effective amount of active compound (s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

As used herein, the term "IL-15:IL-15Rα fusion protein complex" is a complex having IL-15 non-covalently or covalently bound to IL-15Rα. IL-15Rα can be either soluble or membrane bound. In some embodiments, IL-15Rα is the soluble domain of the native IL-15Rα polypeptide. The soluble IL-15Rα can be the IL-15Rα sushi domain or IL-15RαΔE3. In some cases, the soluble IL-15Rα is covalently linked to a biologically active polypeptide and/or to an IgG Fc domain. The IL-15 can be either IL-15 or IL-15 covalently linked to a second biologically active polypeptide. In some cases, IL-15 is covalently bound to the IL-15Rα domain via a linker. The IL-15 can also represent an IL-15 variant comprises one, two, three, four or more amino acid variations relative to a reference sequence. In one embodiment the IL-15 is IL-15N72D. In another embodiment, the IL-15:IL-15Rα fusion protein complex is N-803.

As used herein, the term "immune cells" generally includes white blood cells (leukocytes) which are derived from hematopoietic stem cells (HSC) produced in the bone marrow "Immune cells" includes, e.g., lymphocytes (T cells, B cells, natural killer (NK) cells) and myeloid-derived cells (neutrophil, eosinophil, basophil, monocyte, macrophage, dendritic cells).

The term "immune effector cell," as used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NK-T) cells, mast cells, and myeloid-derived phagocytes. "Immune effector function or immune effector response," as that term is used herein, refers to function or response, e.g., of an immune effector cell, that enhances or promotes an immune attack of a target cell. For example, an immune effector function or response refers a property of a T or NK cell that promotes killing or the inhibition of growth or proliferation, of a target cell. In the case of a T cell, primary stimulation and co-stimulation are examples of immune effector function or response.

The term "immunoregulatory" or "immune cell modulator" is meant a compound, composition or substance that is immunogenic (i.e. stimulates or increases an immune response) or immunosuppressive (i.e. reduces or suppresses an immune response). "Cells of the immune system" or "immune cells", is meant to include any cells of the immune system that may be assayed or involved in mounting an immune response, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types. The functions or responses to an antigen can be measured by any type of assay, e.g. RIA, ELISA, FACS, Western blotting, etc.

The term "induces or enhances an immune response" is meant causing a statistically measurable induction or increase in an immune response over a control sample to which the peptide, polypeptide or protein has not been administered. Conversely, "suppression" of an immune response is a measurable decrease in an immune response over a control sample to which the peptide, polypeptide or protein has been administered, for example, as in the case of suppression of an immune response in an auto-immune scenario. Preferably the induction or enhancement of the immune response results in a prophylactic or therapeutic response in a subject. Examples of immune responses are increased production of type I IFN, increased resistance to viral and other types of infection by alternate pathogens. The enhancement of immune responses to viruses (anti-virus responses), or the development of vaccines to prevent virus infections or eliminate existing viruses.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

By "neoplasia" is meant a disease or disorder characterized by excess proliferation or reduced apoptosis. Neoplastic conditions include, but are not limited to, cancers, sarcomas, tumors, leukemias, lymphomas, and the like. A neoplastic condition refers to the disease state associated with the neoplasia. Colon cancer (e.g., colorectal cancer), lung cancer and ovarian cancer are examples (non-limiting) of a neoplastic condition. Illustrative neoplasms for which the invention can be used include, but are not limited to leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, glioblastoma multiforme, astrocytoma, medulloblastoma, craniopharyngioma, ependymoma, pinealoma, hemangioblastoma, acoustic neuroma, oligodenroglioma, schwannoma, meningioma, melanoma, neuroblastoma, and retinoblastoma). In particular embodiments, the neoplasia is multiple myeloma, beta-cell lymphoma, urothelial/bladder carcinoma or melanoma.

As used herein, "obtaining" as in "obtaining an agent" includes synthesizing, purchasing, or otherwise acquiring the agent.

"Optional" or "optionally" means that the subsequently described event or circumstance can or cannot occur, and that the description includes instances where the event or circumstance occurs and instances where it does not.

As used in this specification and the appended claims, the term "or" is generally employed in its sense including "and/or" unless the content clearly dictates otherwise.

"Parenteral" administration of an immunogenic composition includes, e.g., subcutaneous (s.c.), intravenous (i.v.), intramuscular (i.m.), or intrasternal injection, or infusion techniques.

The terms "preventing" and "prevention" refer to the administration of an agent or composition to a clinically asymptomatic individual who is susceptible or predisposed to a particular adverse condition, disorder, or disease, and thus relates to the prevention of the occurrence of symptoms and/or their underlying cause.

By "reduces" is meant a negative alteration of at least 5%, 10%, 25%, 50%, 75%, or 100%.

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. It will be appreciated that, although not precluded, treating a disorder or condition does not require that the disorder, condition or symptoms associated therewith be completely eliminated.

Treatment of patients with neoplasia may include any of the following: Adjuvant therapy (also called adjunct therapy or adjunctive therapy) to destroy residual tumor cells that may be present after the known tumor is removed by the initial therapy (e.g. surgery), thereby preventing possible cancer reoccurrence; neoadjuvant therapy given prior to the surgical procedure to shrink the cancer; induction therapy to cause a remission, typically for acute leukemia; consolidation therapy (also called intensification therapy) given once a remission is achieved to sustain the remission; maintenance therapy given in lower or less frequent doses to assist in prolonging a remission; first line therapy (also called standard therapy); second (or 3rd, 4th, etc.) line therapy (also called salvage therapy) is given if a disease has not responded or reoccurred after first line therapy; and palliative therapy (also called supportive therapy) to address symptom management without expecting to significantly reduce the cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Certain methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention to a subject. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Genes: All genes, gene names, and gene products disclosed herein are intended to correspond to homologs from any species for which the compositions and methods disclosed herein are applicable. It is understood that when a gene or gene product from a particular species is disclosed, this disclosure is intended to be exemplary only, and is not to be interpreted as a limitation unless the context in which it appears clearly indicates. Thus, for example, for the genes or gene products disclosed herein, are intended to encompass homologous and/or orthologous genes and gene products from other species.

Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All published foreign patents and patent applications cited herein are incorporated herein by reference.

BRIEF DESCRIPTION OF THE DRAWINGS

FIGS. 2A-2F are a series of graphs demonstrating the impact of N-803 on peripheral blood cell subsets. Cryopreserved peripheral blood mononuclear cells were assessed by flow cytometry immediately before (day 0) and at the indicated timepoints after initiation of N-803 treatment. FIG. 2A: The absolute numbers of cells per μL of peripheral blood for each subset was determined by multiplying the percentage of a given cell type (relative to the total $CD45^+$ population) by the overall WBC count. Fold changes in each subset are relative to the baseline (day 0) sample. FIG. 2B: Relative percentages of naïve, central memory (CM), effector memory (EM), and CD45RA-expressing effector memory (EMRA) $CD3^+CD4^+$ or $CD3^+CD8^+$ T cell subsets. FIG. 2C: Relative percentages of $CD3^+CD4^+$ or $CD3^+CD8^+$ T cell subsets expressing the chemokine receptors CD183 (CXCR3), CD194 (CCR4), and/or CD196 (CCR6). The Th1, Th2, and Th17 designated in parentheses are only applicable to the $CD3^+CD4^+$ T cell subset. FIG. 2D: The percentage of $CD3^+CD4^+$ or $CD3^+CD8^+$ T cells expressing cell surface antigens that are altered during T cell activation. CD25, CD38, CD69, and HLA-DR are upregulated while CD28 is downregulated upon T cell activation. FIG. 2E: The percentage of $CD3^+CD4^+$ or $CD3^+CD8^+$ T cells expressing molecules involved in immune checkpoint regulation. FIG. 2F: The percentage of $CD3^+CD4^+$ or $CD3^+CD8^+$ T cells expressing intracellular perforin (Pfn), granzyme B (GzmB) or the proliferation marker K167.

FIG. 4 is a table depicting the demographic characteristics of the patients enrolled in the study. The average age being 43 years old, average CD4⁺ T cell count of 821, the average number of years that the subjects were HIV⁺ was 12 years and the average number of years that the patients were on anti-retroviral therapy was 9.

FIG. 9 is a photograph of an immunostain demonstrating the infiltration of CD20 and CD8 positive cells in a patient after administration of 6 mcg/kg N-803.

FIGS. 10A and 10B are photographs of immunostains demonstrating that N-803 induces homing of NK cells to lymph nodes where latently HIV-infected cells reside. The NK cells can potentially kill HIV-infected cells. FIG. 10A is a CD56 staining of the lymph nodes before N-803 administration. FIG. 10B shows the infiltration of CD56 positive cell into the lymph nodes after a 3$^{rd}$ dose of N-803 (3.0 mcg/kg subcutaneously).

DETAILED DESCRIPTION

Figure 1C:
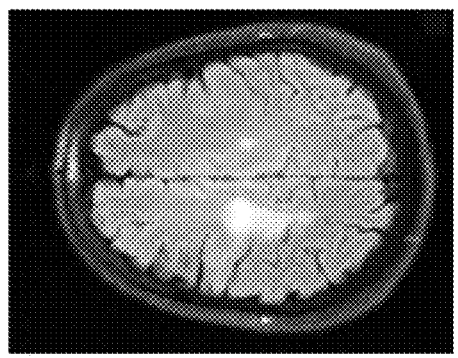
FIGS. 1A-1C are a series of FLAIR MRI images before initiation of N-803 (FIG. 1A), after 2 cycles (FIG. 1B), and after 8 cycles (FIG. 1C), demonstrating improvement in the posterior right frontal subcortical white matter lesion.

The invention is based in part, on the finding that treatment with a novel interleukin-15 (IL-15) super-agonist N-803 was effective in treating immune compromised subjects, such as those infected with human immunodeficiency virus (HIV), tumors and the like. Treatment of subjects with the interleukin-15 (IL-15) super-agonist N-803 was effective in patients infected with JC polyomavirus (JCV). The treatment resulted in decreased JC polyomavirus (JCV) count and neurological improvement in a subject with Progressive Multifocal Leukoencephalopathy (PML) and JC polyomavirus (JCV) in a post-allogeneic hematopoietic stem cell transplant patient (HCT). These results demonstrated that treatment with N-803 increased circulating NK cells, effector memory and effector memory RA T cells. N-803 is a complex of an interleukin-15 (IL-15) superagonist mutant and a dimeric IL-15 receptor α/Fc fusion protein, i.e., an IL-15N72D:IL-15RαSu/Fc complex (N-803).

Thus, described herein are methods of treating immunosuppressed patients, or for treating a neoplasia in a subject. In certain embodiments, a subject is infected with a retrovirus. The retrovirus can be a lentivirus, for example, a human immunodeficiency virus; a simian immunodeficiency virus; a feline immunodeficiency virus; a bovine immunodeficiency virus or Human T-cell leukemia virus. In certain embodiments, an immunosuppressed patient is one who is infected with HIV or any other immunosuppressive virus or disease agent. In one aspect, an immunosuppressed patient is one who has undergone post-allogeneic hematopoietic stem cell transplant (HCT). However, the invention is not just limited to immunosuppressed subjects having undergone HCT, but to any immunosuppressed subject, regardless of cause. In another aspect, a subject is identified as having or at risk of developing a neoplasia. An effective amount of a pharmaceutical composition comprising an IL-15:IL-15Rα complex is administered to the subject, thereby treating the immunosuppressed subject or neoplasia.

In certain embodiments, the soluble fusion protein complexes of the invention include an IL-15 polypeptide, IL-15 variant, or a functional fragment thereof and a soluble IL-15Rα polypeptide or a functional fragment thereof. In some cases, one or both of the IL-15 and IL-15Rα polypeptides further include an immunoglobulin Fc domain or a functional fragment thereof. For example, the IL-15/IL-15Rα complex is an IL-15N72D:IL-15RαSu/Fc complex (N-803), wherein the N-803 comprises a dimeric IL-15RαSu/Fc and two IL-15N72D molecules.

Allogeneic, and in some cases autologous, hematopoietic stem cell transplantation (HCT) is the treatment of choice for many malignant hematological disorders (for reviews of HCT and adoptive cell therapy approaches, see, Rager & Porter, Ther Adv Hematol (2011) 2(6) 409-428; Roddie & Peggs, Expert Opin. Biol. Ther. (2011) 11(4):473-487; Wang et al. Int. J. Cancer: (2015)136, 1751-1768; and Chang, Y. J. and X. J. Huang, Blood Rev, 2013. 27(1): 55-62). The efficacy of allogeneic HCT as a curative option for hematological malignancy is influenced by a number of factors including the underlying disease, the pre-transplant conditioning regimen and the graft-versus-tumor (GVT) effect mediated by donor leukocytes within the graft. The last two factors must be balanced against transplant-related mortality (TRM). For example, reduced intensity conditioning regimens are now being used to provide sufficient immunosuppression for donor cell engraftment without the highly toxic, inflammatory 'cytokine storm' induced by conventional myeloablative conditioning. These less toxic strategies permit use of HCT in a population of previously ineligible patients.

Interleukin-15 (IL-15) is a potent cytokine that increases CD8⁺ T and NK cell numbers and function in experimental models. However, prior to the invention described herein, there were obstacles in using IL-15 therapeutically, specifically its low potency and short in vivo half-life. To help overcome this, an IL-15 superagonist complex (referred to as N-803 or IL-15 SA) comprised of an IL-15N72D mutation and IL-15RαSu/Fc fusion was developed. N-803 exhibits a significantly longer serum half-life, improved biodistribution to the lymphoid organs, and increased in vivo activity against various tumors in animal models.

As described herein, the effects of N-803 in a 27-year-old male with history of T-cell acute lymphoblastic leukemia, status-post allogeneic HCT presented with left-sided weakness progressing to paralysis were evaluated. Brain MM was consistent with PML and CSF PCR was positive for JCV. Treatment with mefloquine and mirtazapine was initiated, with no improvement. N-803 (IL-15N72D:IL-15RαSU/IgG1Fc; N-803), an interleukin-15 super-agonist, was added under compassionate use. After 8 cycles, the CSF JCV DNA copy number decreased, MRI abnormalities improved, and neurologic deficits improved. Flow cytometry of peripheral blood demonstrated increased circulating NK cells, effector memory and effector memory RA cells. This case provides evidence of therapeutic benefit of N-803 in post-allogeneic HCT PML. Thus, as described herein, N-803 is a highly potent compound for increasing circulating immune cell and an immunotherapeutic agent to complement stem cell transplantation and adaptive immunotherapy.

Human Immunodeficiency Virus (HIV). HIV/AIDS remains a major public health problem, as over 40 million people worldwide are infected and new infections continue at greater than two million/year (Adejumo O A, et al. *J Int AIDS Soc* 2015; 18:20049). Combination antiretroviral therapy (cART) effectively controls ongoing viral replication and can restore lost numbers of CD4+ T-cells. However, treatment fails to eliminate virus from latently infected cells (Kulpa D A, Chomont N. *J Virus Erad* 2015; 1:59-66). In subsets of resting CD4+ memory T-cells, integrated proviral DNA persists and can be reactivated to produce replication-competent virus. This can result in rapid viral rebound when cART ceases (Coffin J M. *Science* 1995; 267:483-489; Coffin J M. *AIDS* 1996; 10 (Suppl 3):S75-84). Therefore, infected people must maintain life-long treatment due to viral persistence in cell reservoirs.

Elimination of latent proviral DNA remains enigmatic. During latency, HIV-1-infected cells produce little or no viral proteins, thereby avoiding host antiviral immune clearance or direct viral cytopathicity. Eradication of virus requires its clearance and prevention of re-infection of latently infected cell CD4+ T effector memory cells (Saleh S., et al. *Blood* 2007; 110:4161-4164; Swiggard W J., et al., *J Virol* 2005; 79:141799-14188) amongst other infected lymphocytes and monocyte-macrophages present in spleen, lymph nodes, brain, genitourinary tract and gut to achieve a disease "cure" (Lusic M, Giacca M. *J Mol Biol* 2015; 427:688-694).

Accordingly, in certain embodiments, a method of treating a subject suffering from a human immunodeficiency virus (HIV) infection comprises administering to the subject a composition comprising a therapeutically effective amount of an IL-15:IL-15Rα (N-803) complex, wherein the IL-15:IL-15Rα complex modulates amounts of circulating immune effector cells and/or activates immune effector cells. In embodiments, the IL-15:IL-15Rα complex is an IL-15N72D:IL-15RαSu/Fc complex (N-803) comprising a dimeric IL-15RαSu/Fc and two IL-15N72D molecules. The HIV infection is active or in a latent stage.

The IL-15:IL-15Rα complex can be administered to the subject in escalating therapeutically effective amounts over a period of time to maintain an HIV specific immune response In certain aspects the dose is escalated to a maximum therapeutically effective amount that is the highest possible dose tolerated by the patient. In certain embodiments, the IL-15:IL-15Rα complex is administered until the HIV is undetectable or eradicated from the subject. In certain embodiments, the therapeutically effective amount of the IL-15:IL-15Rα complex is from about 0.01 mcg/kg to about 100.0 mcg/kg. In certain embodiments, the therapeutically effective amount is from about 1 mcg/kg to about 6.0 mcg/kg. In certain embodiments, the routes of administration of the IL-15L-15Rα complex to the subject comprise: subcutaneous, intravenous, intraperitoneal, intramuscular, intratumoral or intradermal routes.

The human immunodeficiency virus can be HIV-1 or HIV-2 or any circulating recombinant form thereof. The genetic variability of HIV is reflected in the multiple groups and subtypes that have been described. A collection of HIV sequences is compiled in the Los Alamos HIV databases and compendiums. The methods and compositions of the invention can be applied to HIV from any of those various groups, subtypes, and circulating recombinant forms. These include for example, the HIV-1 major group (often referred to as Group M) and the minor groups, Groups N, O, and P, as well as but not limited to, any of the following subtypes, A, B, C, D, F, G, H, J and K. or group (for example, but not limited to any of the following Groups, N, O and P) of HIV. The methods and compositions can also be applied to HIV-2 and any of the A, B, C, F or G clades (also referred to as "subtypes" or "groups"), as well as any circulating recombinant form of HIV-2.

The eradication of a retrovirus, such as HIV, from the subject can be determined by, for example, the EDITS (Env Detection by Induced Transcript Sequencing) assay described in the examples section which follows, or by the detection of one or more HIV nuclei acid sequences or peptides e.g. MA (matrix protein, p17); CA (capsid protein, p24); SP1 (spacer peptide 1, p2); NC (nucleocapsid protein, p'7); SP2 (spacer peptide 2, p1) and P6 protein; vif, nef (negative factor) vpu (Virus protein U) and tev; pol, e.g., reverse transcriptase (RT) and RNase H, integrase (IN), and HIV protease (PR); env, e.g., gp160, or a cleavage product of gp160, e.g., gp120 or SU, and gp41 or TM; or tat, e.g., the 72-amino acid one-exon Tat or the 86-101 amino-acid two-exon Tat.

Interleukin-15

IL-15 is a pleiotropic cytokine that plays various roles in the innate and adaptive immune systems, including the development, activation, homing and survival of immune effector cells, especially NK, NK-T and CD8+ T cells (Cooper, M. A., et al., *Blood*, 2001. 97(10): p. 3146-51). IL-15, a member of the common gamma chain (γc) cytokine family, binds to a receptor complex that consists of IL-15Rα, IL-2Rβ and the γc chain (Grabstein, K. H., et al., *Science*, 1994. 264(5161): p. 965-8; Giri, J. G., et al., *Embo J*, 1995. 14(15): p. 3654-63). Furthermore, IL-15 functions as a key regulator of development, homeostasis and activity of NK cells (Prlic, M., et al., *J Exp Med*, 2003. 197(8): p. 967-76; Carson, W. E., et al., *J Clin Invest*, 1997. 99(5): p. 937-43). IL-15 administration to normal mice or overexpression of IL-15 in the transgenic mouse model increases the number and percentage of NK cells in the spleen (Evans, R., et al., *Cell Immunol*, 1997. 179(1): p. 66-73; Marks-Konczalik, J., et al., *Proc Natl Acad Sci USA*, 2000. 97(21): p. 11445-50), the proliferation and survival of NK cells, as well as their cytolytic activity and cytokine secretion. IL-15 administration could also increase the NK cell number and function in recipients of stem cell transplantation (Katsanis, E., et al., *Transplantation*, 1996. 62(6): p. 872-5; Judge, A. D., et al., *J Exp Med*, 2002. 196(7): p. 935-46; Alpdogan, O., et al., *Blood*, 2005. 105(2): p. 865-73; Sauter, C. T., et al., *Bone Marrow Transplantation*, 2013. 48(9): p. 1237-42).

The primary limitations in clinical development of recombinant human IL-15 (rIL-15) are low production yields in standard mammalian cell expression systems and a short serum half-life (Ward, A., et al., *Protein Expr Purif*, 2009. 68(1): p. 42-8; Bessard, A., et al., *Mol Cancer Ther*, 2009. 8(9): p. 2736-45). The formation of the IL-15:IL-15Rα complex, with both proteins co-expressed in the same cell can stimulate immune effector cells bearing the IL-2βγc receptor through a trans-presentation mechanism. In addition, when IL-15 is bound to IL-15Rα, it increased the affinity of the IL-15 to IL-2R13 approximately 150-fold, when compared with free IL-15 (Ring, A. M., et al., *Nat Immunol*, 2012. 13(12): p. 1187-95). A superagonist mutant of IL-15 (IL-15N72D), which has increased IL-2Rβ binding ability (4-5 fold higher than native IL-15) has been identified for therapeutic usages (Zhu, X., et al., Novel human interleukin-15 agonists. *J Immunol*, 2009. 183(6): p. 3598-607). The strong interaction of IL-15N72D and soluble IL-15Rα was exploited to create an IL-15 superagonist complex with IL-15N72D bound to IL-15RαSu/Fc. The soluble fusion protein, IL-15RαSu/Fc, was created by linking the human IL-15RαSu domain with human IgG1 containing the Fc domain. Studies on IL-15:IL-15Rα complexes show an advantage of increased intracellular stability of IL-15 (Bergamaschi, C., et al., *J Biol Chem,* 2008. 283(7): p. 4189-99; Duitman, E. H., et al., *Mol Cell Biol,* 2008. 28(15): p. 4851-61). Co-expression of both the IL-15N72D and IL-15RαSu/Fc proteins resulted in a soluble and stable complex with significantly longer serum half-life and increased biological activity, compared to native IL-15 (Han, K. P., et al., *Cytokine,* 2011. 56(3): p. 804-10). As indicated above, this IL-15N72D:IL-15RαSu/Fc complex (N-803) was >10-fold more active than free IL-15 in promoting in vitro proliferation of IL-15-dependent cells (Zhu, X., et al., Novel human interleukin-15 agonists. *J Immunol,* 2009. 183(6): p. 3598-607). N-803 has potent anti-tumor activity in syngeneic murine models of multiple myeloma (Xu, W., et al., *Cancer Res,* 2013. 73(10): p. 3075-86).

IL-15:IL-15Rα Complex

As defined above, an IL-15:IL-15Rα fusion protein complex can refer to a complex having IL-15 non-covalently bound to the soluble IL-15Rα domain of the native IL-15Rα. In some cases, the soluble IL-15Rα is covalently linked to a biologically active polypeptide and/or to an IgG Fc domain. The IL-15 can be either IL-15 or IL-15 covalently linked to a second biologically active polypeptide. The crystal structure of the IL-15:IL-15Rα complex is shown in Chirifu et al., 2007 *Nat Immunol* 8, 1001-1007, incorporated herein by reference.

In certain embodiments, the IL-15Rα comprises IL-15RαSushi (IL-15RαSu). In other embodiments, the IL-15 is a variant IL-15 (e.g., IL-15N72D).

In certain embodiments of the soluble fusion protein complexes of the invention, the IL-15 polypeptide is an IL-15 variant having a different amino acid sequence than native IL-15 polypeptide. The human IL-15 polypeptide is referred to herein as huIL-15, hIL-15, huIL15, hIL15, IL-15 wild type (wt) and variants thereof are referred to using the native amino acid, its position in the mature sequence and the variant amino acid. For example, huIL15N72D refers to human IL-15 comprising a substitution of N to D at position 72. In certain embodiments, the IL-15 variant functions as an IL-15 agonist as demonstrated, e.g., by increased binding activity for the IL-15RβγC receptors compared to the native IL-15 polypeptide. In certain embodiments, the IL-15 variant functions as an IL-15 antagonist as demonstrated by e.g., decreased binding activity for the IL-15RβγC receptors compared to the native IL-15 polypeptide. In certain embodiments, the IL-15 variant has increased binding affinity or a decreased binding activity for the IL-15RβγC receptors compared to the native IL-15 polypeptide. In certain embodiments, the sequence of the IL-15 variant has at least one (i.e., 1, 2, 3, 4, 5, 6, 7, 8, 9, 10, or more) amino acid change compared to the native IL-15 sequence. The amino acid change can include one or more of an amino acid substitution or deletion in the domain of IL-15 that interacts with IL-15Rβ and/or IL-15RγC. In certain embodiments, the amino acid change is one or more amino acid substitutions or deletions at position 8, 61, 65, 72, 92, 101, 108, or 111 of the mature human IL-15 sequence. For example, the amino acid change is the substitution of D to N or A at position 8, D to A at position 61, N to A at position 65, N to R at position 72 or Q to A at position 108 of the mature human IL-15 sequence, or any combination of these substitutions. In certain embodiments, the amino acid change is the substitution of N to D at position 72 of the mature human IL-15 sequence.

N-803

N-803 comprises an IL-15 mutant with increased ability to bind IL-2Rβγ and enhanced biological activity (U.S. Pat. No. 8,507,222, incorporated herein by reference). This super-agonist mutant of IL-15 was described in a publication (J Immunol 2009 183:3598) and a patent has been issued by the U.S. Patent & Trademark Office on the super agonist and several patents applications are pending (e.g., U.S. Ser. Nos. 12/151,980 and 13/238,925). This IL-15 super-agonist in combination with a soluble IL-15α receptor fusion protein (IL-15RαSu/Fc) results in a protein complex with highly potent IL-15 activity in vitro and in vivo (Han et al., 2011, *Cytokine,* 56: 804-810; Xu, et al., 2013 *Cancer Res.* 73:3075-86, Wong, et al., 2013, *Oncolmmunology* 2:e26442). This IL-15 super agonist complex (IL-15N72D: IL-15RαSu/Fc) is referred to as N-803. Pharmacokinetic analysis indicated that the complex has a half-life of 25 hours following i.v. administration in mice. N-803 exhibits impressive anti-tumor activity against aggressive solid and hematological tumor models in immunocompetent mice. It can be administered as a monotherapy using a twice weekly or weekly i.v. dose regimen or as combinatorial therapy with an antibody. The N-803 anti-tumor response is also durable. Tumor-bearing mice that were cured after N-803 treatment were also highly resistant to re-challenge with the same tumor cells indicating that N-803 induces effective immunological memory responses against the re-introduced tumor cells.

Fc Domain

N-803 comprises an IL-15N72D:IL-15RαSu/Fc fusion complex. Fusion proteins that combine the Fc regions of IgG with the domains of another protein, such as various cytokines and soluble receptors have been reported (see, for example, Capon et al., *Nature,* 337:525-531, 1989; Chamow et al., *Trends Biotechnol.,* 14:52-60, 1996; U.S. Pat. Nos. 5,116,964 and 5,541,087). The prototype fusion protein is a homodimeric protein linked through cysteine residues in the hinge region of IgG Fc, resulting in a molecule similar to an IgG molecule without the heavy chain variable and $C_{H1}$ domains and light chains. The dimeric nature of fusion proteins comprising the Fc domain may be advantageous in providing higher order interactions (i.e. bivalent or bispecific binding) with other molecules. Due to the structural homology, Fc fusion proteins exhibit an in vivo pharmacokinetic profile comparable to that of human IgG with a similar isotype. Immunoglobulins of the IgG class are among the most abundant proteins in human blood, and their circulation half-lives can reach as long as 21 days. To extend the circulating half-life of IL-15 or an IL-15 fusion protein and/or to increase its biological activity, fusion protein complexes containing the IL-15 domain non-covalently bound to IL-15RαSu covalently linked to the Fc portion of the human heavy chain IgG protein have been made (e.g., N-803).

The term "Fc" refers to a non-antigen-binding fragment of an antibody. Such an "Fc" can be in monomeric or multimeric form. The original immunoglobulin source of the native Fc is preferably of human origin and may be any of the immunoglobulins, although IgG 1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms. Fc domains containing binding sites for Protein A, Protein G, various Fc receptors and complement proteins.

In some embodiments, the term "Fc variant" refers to a molecule or sequence that is modified from a native Fc, but still comprises a binding site for the salvage receptor, FcRn. International applications WO 97/34631 (published Sep. 25, 1997) and WO 96/32478 describe exemplary Fc variants, as well as interaction with the salvage receptor, and are hereby incorporated by reference. Thus, the term "Fc variant" comprises a molecule or sequence that is humanized from a non-human native Fc. Furthermore, a native Fc comprises sites that may be removed because they provide structural features or biological activity that are not required for the fusion molecules of the present invention. Thus, in certain embodiments, the term "Fc variant" comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, (7) antibody-dependent cell-mediated cytotoxicity (ADCC), or (8) antibody dependent cellular phagocytosis (ADCP). Fc variants are described in further detail hereinafter.

The term "Fc domain" encompasses native Fc and Fc variant molecules and sequences as defined above. As with Fc variants and native Fc's, the term "Fc domain" includes molecules in monomeric or multimeric form, whether digested from whole antibody or produced by recombinant gene expression or by other means.

Linkers

In some cases, the fusion protein complexes of the invention also include a flexible linker sequence interposed between the IL-15 or IL-15Rα domains. The linker sequence should allow effective positioning of the polypeptide with respect to the IL-15 or IL-15Rα domains to allow functional activity of both domains.

In certain cases, the soluble fusion protein complex has a linker wherein the first polypeptide is covalently linked to IL-15 (or functional fragment thereof) by a polypeptide linker sequence. In other aspects, the soluble fusion protein complex as described herein has a linker wherein the second polypeptide is covalently linked to IL-15Rα polypeptide (or functional fragment thereof) by polypeptide linker sequence.

The linker sequence is preferably encoded by a nucleotide sequence resulting in a peptide that can effectively position the binding groove of a TCR molecule for recognition of a presenting antigen or the binding domain of an antibody molecule for recognition of an antigen. As used herein, the phrase "effective positioning of the biologically active polypeptide with respect to the IL-15 or IL-15Rα domains", or other similar phrase, is intended to mean the biologically active polypeptide linked to the IL-15 or IL-15Rα domains is positioned so that the IL-15 or IL-15Rα domains are capable of interacting with each other to form a protein complex. For example, the IL-15 or IL-15Rα domains are effectively positioned to allow interactions with immune cells to initiate or inhibit an immune reaction, or to inhibit or stimulate cell development.

The fusion protein complexes of the invention preferably also include a flexible linker sequence interposed between the IL-15 or IL-15Rα domains and the immunoglobulin Fc domain. The linker sequence should allow effective positioning of the Fc domain, biologically active polypeptide and IL-15 or IL-15Rα domains to allow functional activity of each domain. For example, the Fc domains are effectively positioned to allow proper fusion protein complex formation and/or interactions with Fc receptors on immune cells or proteins of the complement system to stimulate Fc-mediated effects including opsonization, cell lysis, degranulation of mast cells, basophils, and eosinophils, and other Fc receptor-dependent processes; activation of the complement pathway; and enhanced in vivo half-life of the fusion protein complex.

Linker sequences can also be used to link two or more polypeptides of the biologically active polypeptide to generate a single-chain molecule with the desired functional activity.

Preferably, the linker sequence comprises from about 7 to 20 amino acids, more preferably from about 10 to 20 amino acids. The linker sequence is preferably flexible so as not hold the biologically active polypeptide or effector molecule in a single undesired conformation. The linker sequence can be used, e.g., to space the recognition site from the fused molecule. Specifically, the peptide linker sequence can be positioned between the biologically active polypeptide and the effector molecule, e.g., to chemically cross-link same and to provide molecular flexibility. The linker preferably predominantly comprises amino acids with small side chains, such as glycine, alanine and serine, to provide for flexibility. Preferably, about 80 or 90 percent or greater of the linker sequence comprises glycine, alanine or serine residues, particularly glycine and serine residues.

Different linker sequences could be used including any of a number of flexible linker designs that have been used successfully to join antibody variable regions together (see, Whitlow, M. et al., (1991) Methods: A Companion to Methods in Enzymology, 2:97-105).

```
Fusions Protein Complexes
The invention provides N-803, which is a protein complex between IL-15N72D
and IL-15RαSu/Fc. An exemplary IL-15N72D nucleic acid sequence is provided below (with
leader peptide) (SEQ ID NO: 1):
(Leader peptide)
atggagacagacacactcctgttatgggtactgctgctctgggttccaggttccaccggt- (IL-15N72D)
aactgggtgaatgtaataagtgatttgaaaaaaattgaagatcttattcaatctatgcatattgatgctactttatatacgga aagtgatgttcaccccagttgcaaagtaacagcaatgaagtgctttctcttggagttacaagttatttcacttgagtccggagatgcaa gtattcatgatacagtagaaaatctgatcatcctagcaaacgacagtttgtcttctaatgggaatgtaacagaatctggatgcaaagaa tgtgaggaactggaggaaaaaaatattaaagaattttttgcagagttttgtacatattgtccaaatgttcatcaacacttct (Stop codon)
taa
```

-continued

An exemplary IL-15N72D amino acid sequence is provided below (with leader peptide)
(SEQ ID NO: 2):
(Leader peptide)
METDTLLLWVLLLWVPGSTG- (IL-15N72D)
NWVNVISDLKKIEDLIQSMHIDATLYTESDVHPSCKVTAMKCFLLELQVISLESG

DASIHDTVENLIILANDSLSSNGNVTESGCKECEELEEKNIKEFLQSFVHIVQMFINTS

In some cases, the leader peptide is cleaved from the mature IL-15N72D
polypeptide (SEQ ID NO: 3):
(IL-15N72D)
NWVNVISDLKKIEDLIQSMHIDATLYTESDVHPSCKVTAMKCFLLELQVISLESG

DASIHDTVENLIILANDSLSSNGNVTESGCKECEELEEKNIKEFLQSFVHIVQMFINTS

An exemplary IL-15RαSu/Fc nucleic acid sequence (with leader peptide) is
provided below (SEQ ID NO: 4):
(Leader peptide)
atggacagacttacttcttcattcctgctcctgattgtccctgcgtacgtcttgtcc- (IL-15RαSu)
atcacgtgccctccccccatgtccgtggaacacgcagacatctgggtcaagagctacagcttgtactccagggagcg gtacatttgtaactctggtttcaagcgtaaagccggcacgtccagcctgacggagtgcgtgttgaacaaggccacgaatgtcgcccactg gacaaccccagtctcaaatgtattaga- (IgG1 CH2-CH3 (Fc domain))
gagcccaaatcttgtgacaaaactcacacatgcccaccgtgcccagcacctgaactcctggggggaccgtcagtctt cctcttccccccaaaacccaaggacaccctcatgatctcccggacccctgaggtcacatgcgtggtggtggacgtgagccacgaagaccc tgaggtcaagttcaactggtacgtggacggcgtggaggtgcataatgccaagacaaagccgcgggaggagcagtacaacagcacgtac cgtgtggtcagcgtcctcaccgtcctgcaccaggactggctgaatggcaaggagtacaagtgcaaggtctccaacaaagccctcccagcc cccatcgagaaaaccatctccaaagccaaagggcagccccgagaaccacaggtgtacaccctgcccccatcccgggatgagctgacca agaaccaggtcagcctgacctgcctggtcaaaggcttctatcccagcgacatcgccgtggagtgggagagcaatgggcagccggagaac aactacaagaccacgcctcccgtgctggactccgacggctccttcttcctctacagcaagctcaccgtggacaagagcaggtggcagcag gggaacgtcttctcatgctccgtgatgcatgaggctctgcacaaccactacacgcagaagagcctctccctgtctccgggtaaa- (Stop codon)
taa An exemplary IL-15RαSu/Fc amino acid sequence (with leader peptide) is
provided below (SEQ ID NO: 5):
(Leader peptide)
MDRLTSSFLLLIVPAYVLS- (IL-15RαSu)
ITCPPPMSVEHADIWVKSYSLYSRERYICNSGFKRKAGTSSLTECVLNKAT

NVAHWTTPSLKCIR- (IgG1 CH2-CH3 (Fc domain))
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKS

LSLSPGK

In some cases, the mature IL-15RαSu/Fc protein lacks the leader sequence
(SEQ ID NO: 6):
(IL-15RαSu)
ITCPPPMSVEHADIWVKSYSLYSRERYICNSGFKRKAGTSSLTECVLNKAT

NVAHWTTPSLKCIR- (IgG1 CH2-CH3 (Fc domain))
EPKSCDKTHTCPPCPAPELLGGPSVFLFPPKPKDTLMISRTPEVTCVVVDV

SHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKS

LSLSPGK

Anti-Cancer Therapeutic Agents

The methods of the invention may include administration of second therapeutic agent or treatment with a second therapy (e.g., a therapeutic agent or therapy that is standard in the art). Exemplary therapeutic agents include chemotherapeutic agents. A "chemotherapeutic agent" is a chemical compound useful in the treatment of cancer. Examples of chemotherapeutic agents include Erlotinib (TARCEVA™, Genentech/OSI Pharm.), Bortezomib (VELCADE™, Millennium Pharm.), Fulvestrant (FASLODEX™, Astrazeneca), Sutent (SU11248, Pfizer), Letrozole (FEMARA™, Novartis), Imatinib mesylate (GLEEVEC™, Novartis), PTK787/ZK 222584 (Novartis), Oxaliplatin (Eloxatin™, Sanofi), 5-FU (5-fluorouracil), Leucovorin, Rapamycin (Sirolimus, RAPAMUNE™, Wyeth), Lapatinib (GSK572016, GlaxoSmithKline), Lonafarnib (SCH 66336), Sorafenib (BAY43-9006, Bayer Labs.), and Gefitinib (IRESSA™, Astrazeneca), AG1478, AG1571 (SU 5271; Sugen), alkylating agents such as Thiotepa and CYTOXAN™ cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin omega 1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN™ doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK™ polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL™ paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE™ doxetaxel (Rhone-Poulenc Rorer, Antony, France); chloranbucil; GEMZAR™ gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX™ (tamoxifen)), raloxifene, droloxifene, 4-hydroxytamoxifen, trioxifene, keoxifene, LY117018, onapristone, and FARESTON™ (toremifene); (ii) aromatase inhibitors that inhibit the enzyme aromatase, which regulates estrogen production in the adrenal glands, such as, for example, 4(5)-imidazoles, aminoglutethimide, MEGASE™ (megestrol acetate), AROMASIN™ (exemestane), formestanie, fadrozole, RIVISOR™ (vorozole), FEMARA™ (letrozole), and ARIMIDEX™ (anastrozole); (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberrant cell proliferation, such as, for example, PKC-alpha, Ralf and H-Ras; (viii) ribozymes such as a VEGF expression inhibitor (e.g., ANGIOZYME™ (ribozyme)) and a HER2 expression inhibitor; (ix) vaccines such as gene therapy vaccines, for example, ALLOVECTIN™ vaccine, LEUVECTIN™ vaccine, and VAXID™ vaccine; PROLEUKIN™ rIL-2; LURTOTECAN™ topoisomerase 1 inhibitor; ABARELIXT™ rmRH; (x) anti-angiogenic agents such as bevacizumab (AVASTIN™, Genentech); and (xi) pharmaceutically acceptable salts, acids or derivatives of any of the above.

Checkpoint Inhibitors

The compositions embodied herein, can also include one or more checkpoint inhibitors. In one embodiment, the subject can be administered an agent which enhances the activity of an immune effector cell. For example, in one embodiment, the agent can be an agent which inhibits a molecule that modulates or regulates, e.g., inhibits, immune response of an immune effector cell, e.g., T cell function. In some embodiments, the molecule that modulates or regulates immune response of an immune effector cell, e.g., T cell function, is an inhibitory molecule, also known as a checkpoint inhibitor. Inhibitory molecules, also referred to herein as checkpoint inhibitors, e.g., Programmed Death 1 (PD-1), can, in some embodiments, decrease the ability of an immune effector cell to mount an immune effector response. Examples of inhibitory molecules include PD-1, PD-L1, CTLA4, TIM3, CEACAM (e.g., CEACAM-1, CEACAM-3 and/or CEACAM-5), LAG3, VISTA, BTLA, TIGIT, LAIR1, CD160, 2B4, CD80, CD86, B7-H3 (CD276), B7-H4 (VTCN1), HVEM (TNFRSF14 or CD270), KIR, A2aR, MHC class I, MHC class II, GAL9, adenosine, and TGFR beta. Inhibition of a molecule that modulates or regulates, e.g., inhibits, T cell function, e.g., by inhibition at the DNA, RNA or protein level, can optimize an immune response. In embodiments, an agent, e.g., an inhibitory nucleic acid, e.g., an inhibitory nucleic acid, e.g., a dsRNA, e.g., an siRNA or shRNA, a clustered regularly interspaced short palindromic repeats (CRISPR), a transcription-activator like effector nuclease (TALEN), or a zinc finger endonuclease (ZFN), can be used to inhibit expression of an inhibitory molecule that inhibits the activity of the immune effector cell. In an embodiment, the inhibitor is an shRNA.

In an embodiment, the agent that modulates or regulates, e.g., inhibits, T-cell function is inhibited within the immune effector cell, e.g. T cell, or immune cell producing that component e.g. immunosuppressive molecule. In these embodiments, a dsRNA molecule that inhibits expression of a molecule that modulates or regulates, e.g., inhibits, T-cell function is linked to the nucleic acid that encodes that component. In an embodiment, a nucleic acid molecule that encodes a dsRNA molecule that inhibits expression of the molecule that modulates or regulates, e.g., inhibits, T-cell function is operably linked to a promoter, e.g., a H1- or a U6-derived promoter such that the dsRNA molecule that inhibits expression of the molecule that modulates or regulates, e.g., inhibits, T-cell function is expressed, e.g., is expressed within a CAR-expressing cell. See e.g., Tiscornia G., "Development of Lentiviral Vectors Expressing siRNA," Chapter 3, in Gene Transfer: Delivery and Expression of DNA and RNA (eds. Friedmann and Rossi). Cold Spring Harbor Laboratory Press, Cold Spring Harbor, N.Y., USA, 2007; Brummelkamp T R, et al. (2002) *Science* 296: 550-553; Miyagishi M, et al. (2002) *Nat. Biotechnol.* 19: 497-500. In an embodiment the nucleic acid molecule that encodes a dsRNA molecule that inhibits expression of the molecule that modulates or regulates, e.g., inhibits, T-cell function is present on the same vector, e.g., a lentiviral vector. In such an embodiment, the nucleic acid molecule that encodes a dsRNA molecule that inhibits expression of the molecule that modulates or regulates, e.g., inhibits, T-cell function is located on the vector, e.g., a lentiviral vector, 5'- or 3'- to the nucleic acid that encodes a component. Examples of dsRNA molecules useful for inhibiting expression of a molecule that modulates or regulates, e.g., inhibits, T-cell function, wherein the molecule that modulates or regulates, e.g., inhibits, T-cell function is PD-1 include RNAi agents that target PD-1.

In one embodiment, the agent that modulates or regulates, e.g., inhibits, T-cell function can be, e.g., an antibody or antibody fragment that binds to an inhibitory molecule. For example, the agent can be an antibody or antibody fragment that binds to PD-1, PD-L1, PD-L2 or CTLA4 (e.g., ipilimumab (also referred to as MDX-010 and MDX-101, and marketed as YERVOY™; Bristol-Myers Squibb; Tremelimumab (IgG2 monoclonal antibody available from Pfizer, formerly known as ticilimumab, CP-675,206). In an embodiment, the agent is an antibody or antibody fragment that binds to TIM3. In an embodiment, the agent is an antibody or antibody fragment that binds to LAG3.

PD-1 is an inhibitory member of the CD28 family of receptors that also includes CD28, CTLA-4, ICOS, and BTLA. PD-1 is expressed on activated B cells, T cells and myeloid cells (Agata et al. 1996 *Int. Immunol* 8:765-75). Two ligands for PD-1, PD-L1 and PD-L2 have been shown to downregulate T cell activation upon binding to PD-1 (Freeman et a. 2000 *J Exp Med* 192:1027-34; Latchman et al. 2001 *Nat Immunol* 2:261-8; Carter et al. 2002 *Eur J Immunol* 32:634-43). PD-L1 is abundant in human cancers (Dong et al. 2003 *J Mot Med* 81:281-7; Blank et al. 2005 *Cancer Immunol. Immunother* 54:307-314; Konishi et al. 2004 *Clin Cancer Res* 10:5094). Immune suppression can be reversed by inhibiting the local interaction of PD-1 with PD-L1. Antibodies, antibody fragments, and other inhibitors of PD-1, PD-L1 and PD-L2 are available in the art and may be used combination with a cars of the present disclosure described herein. For example, nivolumab (also referred to as BMS-936558 or MDX1106; Bristol-Myers Squibb) is a fully human IgG4 monoclonal antibody which specifically blocks PD-1. Nivolumab (clone 5C4) and other human monoclonal antibodies that specifically bind to PD-1 are disclosed in U.S. Pat. No. 8,008,449 and WO2006/121168. Pembrolizumab (formerly known as lambrolizumab, and also referred to as MK03475; Merck) is a humanized IgG4 monoclonal antibody that binds to PD-1. Pembrolizumab and other humanized anti-PD-1 antibodies are disclosed in U.S. Pat. No. 8,354,509 and WO2009/114335 MEDI4736 (Medimmune) is a human monoclonal antibody that binds to PDL1, and inhibits interaction of the ligand with PD1. MDPL3280A (Genentech/Roche) is a human Fc optimized IgG1 monoclonal antibody that binds to PD-L. MDPL3280A and other human monoclonal antibodies to PD-L1 are disclosed in U.S. Pat. No. 7,943,743 and U.S Publication No.: 20120039906. Other anti-PD-L1 binding agents include YW243.55.S70 (heavy and light chain variable regions are shown in SEQ ID NOs 20 and 21 in WO2010/077634) and MDX-1 105 (also referred to as BMS-936559, and, e.g., anti-PD-L1 binding agents disclosed in WO2007/005874). AMP-224 (B7-DCIg; Amplimmune; e.g., disclosed in WO2010/027827 and WO2011/066342), is a PD-L2 Fc fusion soluble receptor that blocks the interaction between PD-1 and B7-H1. Other anti-PD-1 antibodies include AMP 514 (Amplimmune), among others, e.g., anti-PD-1 antibodies disclosed in U.S. Pat. No. 8,609,089, US 2010028330, and/or US 20120114649.

TIM3 (T cell immunoglobulin-3) also negatively regulates T cell function, particularly in IFNγ-secreting CD4$^+$ T helper 1 and CD8$^+$T cytotoxic 1 cells, and plays a critical role in T cell exhaustion. Inhibition of the interaction between TIM3 and its ligands, e.g., galectin-9 (Gal9), phosphotidylserine (PS), and HMGB1, can increase immune response. Antibodies, antibody fragments, and other inhibitors of TIM3 and its ligands are available in the art. For example, antibodies, antibody fragments, small molecules, or peptide inhibitors that target TIM3 binds to the IgV domain of TIM3 to inhibit interaction with its ligands. Antibodies and peptides that inhibit TIM3 are disclosed in WO2013/006490 and US20100247521. Other anti-TIM3 antibodies include humanized versions of RMT3-23 (disclosed in Ngiow et al., 2011, *Cancer Res,* 71:3540-3551), and clone 8B.2C12 (disclosed in Monney et al., 2002, *Nature,* 415:536-541). Bi-specific antibodies that inhibit TIM3 and PD-1 are disclosed in US20130156774.

LAG3 (lymphocyte activation gene-3 or CD223) is a cell surface molecule expressed on activated T cells and B cells that has been shown to play a role in CD8+ T cell exhaustion. Antibodies, antibody fragments, and other inhibitors of LAG3 and its ligands are available in the art. For example, BM S-986016 (Bristol-Myers Squib) is a monoclonal antibody that targets LAG3. IMP701 (Immutep) is an antagonist LAG3 antibody and IMP731 (Immutep and GlaxoSrnithKline) is a depleting LAG3 antibody. Other LAG3 inhibitors include IMP321 (Immutep), which is a recombinant fusion protein of a soluble portion of LAG3 and Ig that binds to MHC class II molecules and activates antigen presenting cells (APC). Other antibodies are disclosed, e.g., in WO02010/019570.

Markers of Human Peripheral Blood Mononuclear Cells (PBMC)

Human peripheral blood mononuclear cells (PBMC) are comprised of complex populations of T cells, B cells, NK cells, monocytes, and dendritic cells. In addition, there are more complicated cell types such as NKT cells that are thought of as T cells that share many properties of NK cells. Within all of these basic populations are many functionally unique subsets. Among the sub-types and subpopulations of T cells and/or of CD4$^+$ and/or of CD8$^+$ T cells are naive T ($T_N$) cells, effector T cells ($T_{EFF}$), memory T cells and sub-types thereof, such as stem cell memory T ($T_{SCMX}$ central memory T ($T_{CM}$ effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as $T_H1$ cells, $T_H2$ cells, $T_H3$ cells, $T_H17$ cells, $T_H9$ cells, $T_H22$ cells, follicular helper T cells, alpha/beta T cells, and delta/gamma T cells.

The major class of T cells is defined by its surface expression of the αβ TCR. This receptor has evolved primarily to recognize peptide antigens presented in a complex with class I or class II MHC proteins. αβ-T cells differentiate into several different subsets, some of which (CD8$^+$ T cells) act primarily to kill cells infected with intracellular microbes, and others (CD4$^+$ T cells) act primarily to regulate the cellular and humoral immune responses. A small subset of αβ-T cells which expresses the NK1.1 (CD161) NK cell antigen (NK-T cells) are usually CD4 and CD8 double negative, recognize glycolipid antigens presented by the CD1d molecule, and appear to be immunoregulatory based on their ability to release rapidly large quantities of the cytokines IFN-γ, IL-4, granulocyte-macrophage colony stimulating factor (GM-CSF), TNF, and others.

CD3, a T cell specific marker, is necessary to differentiate T cells from other populations, since CD4 and CD8 can be expressed by other cell types. CD8 can be expressed on NK cells, while CD4 can be expressed on populations of monocytes and dendritic cells. CD4 and CD8 are also necessary markers for identification of these two major T cell populations.

CD4 and CD8 T cells are most simply classified as naïve or antigen experienced populations including central memory, effector memory and effectors. Central memory and effector memory populations are known to differ in their effector functions and ability to home to different anatomical sites. Two markers are necessary to differentiate naive, central memory, effector memory and effector T cell populations present in PBMC.

The first is CD45, a protein tyrosine phosphatase regulating src-family kinases, is expressed on all hematopoietic cells. CD45 can be expressed as one of several isoforms by alternative splicing of exons that comprise the extracellular domain. CD45RA is expressed on naïve T cells, as well as the effector cells in both CD4 and CD8. After antigen experience, central and effector memory T cells gain expression of CD45RO and lose expression of CD45RA. Thus either CD45RA or CD45RO is used to generally differentiate the naïve from memory populations.

However, differentiation between central and effector memory populations and between naïve and effector populations can be achieved by adding a second marker. There are several markers that have been used for this purpose and these tend to mark these populations at slightly different stages of the differentiation pathway that is thought to occur in T cells as they change from central to effector memory cells. The chemokine receptor CCR7 is considered the gold standard for this discrimination, and the lymph node homing receptor CD62L is a close second choice. Naïve and central memory cells express these receptors in order to migrate to secondary lymphoid organs, while the absence of these receptors allows for effector memory and effector cells to accumulate in peripheral tissues.

In summary, naïve T cells are CD45RA$^+$CD45RO$^-$CCR7$^+$CD62L$^+$, central memory T cells are CD45RA$^-$CD45RO$^+$CCR7$^+$CD62L$^+$, effector memory T cells are CD45RA$^-$CD45RO$^+$CCR7$^-$CD62L$^-$, and effector cells are CD45RA$^+$CD45RO$^-$CCR7$^-$CD62L$^-$.

Following antigen exposure, CD4$^+$ and CD8$^+$ T cells undergo differentiation thorough various stages. The current mainstream hypothesis is that naïve cells ($T_N$) progress through central memory ($T_{CM}$), then effector memory ($T_{EM}$), then finally terminally differentiated effector memory ($T_{EMRA}$) states. Expression of surface markers have been used to identify human T cells in these various states, including CD45RA, CD45RO, CCR7, CD62L, CD27, and CD28. After antigen exposure, naïve T cells, which are CD45RA$^+$CD45RO$^-$CCR7$^+$CD62L$^+$CD27$^+$CD28$^+$ lose expression of CD45RA and gain expression of CD45RO. As memory T cells progress from $T_{CM}$ to $T_{EM}$ cells, they additionally lose expression of CCR7, CD45RA+, CD27, and CD28. Finally, $T_{EMRA}$ cells regain expression of CD45RA, but remain identifiable from naïve T cells by their lack of CCR7, CD62L, CD27, and CD28 expression.

The function of CD4+ $T_{EMRA}$ cells parallels that of CD8+ $T_{EMRA}$ cells. These cells are cytolytic and express IFN-gamma after activation through their TCR or stimulation with PMA/ionomycin. CD4+ $T_{EMRA}$ cells also have shorter telomeres than naïve, $T_{CM}$, and TEM populations, and lower homeostatic proliferation capacity.

Memory T cells are heterogeneous in terms of their phenotype and functional properties. Immunological memory is a fundamental feature of the adaptive immune system. It enables the immune system to respond more rapidly and vigorously to infectious pathogens that have been encountered previously. In particular, memory CD8 T cells play a major role in host defense by rapid recognition and lysis of virus-infected cells. A memory response differs both quantitatively and qualitatively from a primary response. Thus, compared with a naïve population, the precursor frequency of Ag-specific memory cells is increased and, furthermore, these cells have an enhanced capacity to respond to Ag.

Within human CD8 T cells, van Lier and colleagues (Hamann, D., et al., 1997. Phenotypic and functional separation of memory and effector human CD8+ T cells. *J. Exp. Med.* 186:1407-1418) first demonstrated the presence of phenotypically and functionally distinct subsets of primed T cells by analyzing expression of CD27 and CD45RA. Although naïve CD8 T cells express both of these cell surface glycoproteins, cells expressing CD27 but not CD45RA were reported to have functional properties suggestive of "memory" cells and those that expressed CD45RA but not CD27 had functional properties suggestive of "effector" cells.

Subsequently, Lanzavecchia and coworkers (Sallusto, F., et al., 1999. Two subsets of memory T lymphocytes with distinct homing potentials and effector functions. *Nature* 401:708-712; Sallusto, F., et al., 2004. Central memory and effector memory T cell subsets: function, generation, and maintenance. *Annu. Rev. Immunol.* 22:745-763) used expression of CCR7 and CD45RA to define subsets of CD8 T cells. According to this scheme, naïve T cells ($T_N$) express both CCR7 and CD45RA whereas primed CD8 T cells can be considered as belonging to one of three different subsets. Two of these lack expression of CD45RA and thus lie broadly within the van Lier memory subset. Of these, central memory cells ($T_{CM}$) express CCR7 while effector memory ($T_{EM}$) cells lack expression of CCR7. In humans, but not in mice, there is a third T cell memory subset, $T_{EMRA}$, that includes cells that express CD45RA but lack expression of CCR7.

$T_{CM}$ and $T_{EM}$ can be distinguished by their different homing and effector capacities (Sallusto, F., et al., 2004). Like naïve cells, $T_{CM}$ express CD62 ligand (CD62L) and CCR7 and home to secondary lymphoid organs. In contrast, expression of a different set of chemokine receptors (e.g., CXCR3) allows $T_{EM}$ and $T_{EMRA}$ to gain access to inflamed peripheral tissues. Human $T_{EM}$ and $T_{EMRA}$ in particular, are more differentiated in terms of effector function than $T_{CM}$. They display potent ex vivo cytotoxicity and produce Th1 cytokines upon stimulation, whereas $T_{CM}$ mainly produce IL-2 and Th2 cytokines. Further studies have shown that $T_{CM}$ have a higher proliferative potential and greater resistance to apoptosis, whereas $T_{EM}/T_{EMRA}$ have a skewed TCR repertoire and are characterized by a "senescent" replicative history (Geginat, J., A. Lanzavecchia, F. Sallusto. 2003. Proliferation and differentiation potential of human CD8+ memory T-cell subsets in response to antigen or homeostatic cytokines. *Blood* 101:4260.-4266; Zippelius, A., et al., 2004. Human thymus exports naïve CD8 T cells that can home to nonlymphoid tissues. *J. Immunol.* 172:2773-2777; Huster, K. M., et al., 2004. Selective expression of IL-7 receptor on memory T cells identifies early CD40L-dependent generation of distinct CD8+ memory T cell subsets. *Proc. Natl. Acad. Sci. USA* 101:5610-5615).

The importance of both $T_{CM}$ and $T_{EM}$ subsets for the control of infectious diseases and the effectiveness of vaccines has been shown in several murine studies (Lauvau, G., et al., 2001. Priming of memory but not effector CD8 T cells by a killed bacterial vaccine. *Science* 294:1735-1739; Zaph, C., et al., 2004. Central memory T cells mediate long-term immunity to Leishmania major in the absence of persistent parasites. *Nat. Med.* 10:1104-1110. Seaman, M. S., et al., 2004. Subsets of memory cytotoxic T lymphocytes elicited by vaccination influence the efficiency of secondary expansion in vivo. *J. Virol.* 78:206-215). In mice, Ahmed and colleagues (Wherry, E. J., et al., .2003. Lineage relationship and protective immunity of memory CD8 T cell subsets. *Nat. Immunol.*4:225.-234) have demonstrated a linear differentiation pathway $T_N \rightarrow$effector$\rightarrow T_{EM} \rightarrow T_{CM}$ following acute lymphocytic choriomeningitis virus (LCMV) infection.

Adoptive Cell Therapy

Adoptive cell therapy (ACT) (including allogeneic and autologous hematopoietic stem cell transplantation (HSCT) and recombinant cell (i.e., CAR T) therapies) is the treatment of choice for many malignant disorders (for reviews of HSCT and adoptive cell therapy approaches, see, Rager & Porter, *Ther Adv Hematol* (2011) 2(6) 409-428; Roddie & Peggs, *Expert Opin. Biol. Ther.* (2011) 11(4):473-487; Wang et al. Int. *J. Cancer.* (2015)136, 1751-1768; and Chang, Y. J. and X. J. Huang, *Blood Rev,* 2013. 27(1): 55-62). Such adoptive cell therapies include, but are not limited to, allogeneic and autologous hematopoietic stem cell transplantation, donor leukocyte (or lymphocyte) infusion (DLI), adoptive transfer of tumor infiltrating lymphocytes, or adoptive transfer of T cells or NK cells (including recombinant cells, i.e., CAR T, CAR NK, gene-edited T cells or NK cells, see Hu et al. *Acta Pharmacologica Sinica* (2018) 39: 167-176, Irving et al. *Front Immunol.* (2017) 8: 267). Beyond the necessity for donor-derived cells to reconstitute hematopoiesis after radiation and chemotherapy, immunologic reconstitution from transferred cells is important for the elimination of residual tumor cells. The efficacy of ACT as a curative option for malignancies is influenced by a number of factors including the origin, composition and phenotype (lymphocyte subset, activation status) of the donor cells, the underlying disease, the pre-transplant conditioning regimen and post-transplant immune support (i.e., IL-2 therapy) and the graft-versus-tumor (GVT) effect mediated by donor cells within the graft. Additionally, these factors must be balanced against transplant-related mortality, typically arising from the conditioning regimen and/or excessive immune activity of donor cells within the host (i.e., graft-versus-host disease, cytokine release syndrome, etc.).

Approaches utilizing adoptive NK cell therapy have become of significant interest. In patients receiving autologous HSCT, blood NK cell numbers recover very early after the transplant and the levels of NK cells correlate with a positive outcome (Rueff et al., 2014, *Biol. Blood Marrow Transplant.* 20, 896-899). Although therapeutic strategies with autologous NK cell transfer have had limited success due to a number of factors, adoptive transfer of ex vivo-activated allogeneic (or haplo-identical) NK cells has emerged as a promising immunotherapeutic strategy for cancer (Guillerey et al. 2016. *Nature Immunol.* 17: 1025-1036). The activity of these cells is less likely to be suppressed by self-MHC molecules compared to autologous NK cells. A number of studies have shown that adoptive therapy with haploidentical NK cells to exploit alloreactivity against tumor cells is safe and can mediate significant clinical activity in AML patients. Taking these findings further, recent studies have focused on optimizing ex vivo activation/expansion methods for NK cells or NK precursors (i.e., stem cells) and pre-transplant conditioning and post-transplant immune support strategies; use of NK cell lines or recombinant tumor-targeting NK cells; evaluation of combination therapies with other agents such as therapeutic Ab, immunomodulatory agents (lenalidomide), and anti-KIR and checkpoint Abs. In each case, these strategies could be complemented by the combination therapeutic approach of the invention, which has the capacity to augment NK cell proliferation and activation.

Natural Killer Cells: One of the major types of circulating mononuclear cells is that of the natural killer, or NK, cell (M. Manoussaka et al., *Journal of Immunology* 158:112-119, 1997). Originally defined based on their ability to kill certain tumors and virus-infected cells, NK cells are now known as one of the components of the early, innate immune system. In addition to their cytotoxic capabilities, NK cells serve as regulators of the immune response by releasing a variety of cytokines. In addition, the generation of complex immune responses is facilitated by the direct interaction of NK cells with other cells via various surface molecules expressed on the NK cells.

NK cells are derived from bone marrow precursors (O. Haller et al., *Journal of Experimental Medicine* 145:1411-1420, 1977). NK cells appear to be closely related to T cells, and the two cell types share many cell surface markers (M. Manoussaka et al., 1997). As noted above, these cell surface markers play a significant role in NK cell activity. For example, murine NK cells express specific antigens on their surfaces, such as asialo GM1, NK1, and NK2 antigens (D. See et al., *Scand. J. Immunol.* 46:217-224, 1997), and the administration of antibodies against these antigens results in depletion of NK cells in vivo (Id.).

Similarly to cytotoxic T lymphocytes (CTL), NK cells exert a cytotoxic effect by lysing a variety of cell types (Srivastava, S., Lundqvist, A. & Childs, R. W. Natural killer cell immunotherapy for cancer: a new hope. *Cytotherapy* 10, 775-783; 2008). These include normal stem cells, infected cells, and transformed cells. The lysis of cells occurs through the action of cytoplasmic granules containing proteases, nucleases, and perforin. Cells that lack MHC class I are also susceptible to NK cell-mediated lysis (H. Reyburn et al., *Immunol. Rev.* 155:119-125, 1997). In addition, NK cells exert cytotoxicity in a non-MHC restricted fashion (E. Ciccione et al., *J. Exp. Med.* 172:47, 1990; A. Moretta et al., *J. Exp. Med.* 172:1589, 1990; and E. Ciccione et al., *J. Exp. Med.* 175:709). NK cells can also lyse cells by antibody-dependent cellular cytotoxicity.

As noted above, NK cells mediate some of their functions through the secretion of cytokines, such as interferon γ (IFN-γ), granulocyte-macrophage colony-stimulating factors (GM-CSFs), tumor necrosis factor α (TNF-α), macrophage colony-stimulating factor (M-CSF), interleukin-3 (IL-3), and IL-8. NK cell cytotoxic activity is regulated through a balance of activating and inhibitory receptors that enables fine-tuned control of cytotoxic activity, preventing cytotoxicity against healthy cells, while maintaining effective cytotoxic capacity against tumor cells. Indeed, multiple studies have demonstrated the safety of adoptive NK cell transfer and clinical anti-cancer effects, highlighting the potential for NK cells as an effective cancer immunotherapy ((Parkhurst, M. R., et al. *Clin Cancer Res* 17, 6287-6297 (2011); Ruggeri, L. et al. *Science* 295,2097-2100, (2002); Miller, J. S. et al. *Blood* 105,3051-3057, (2005; Bachanova, V. et al. *Blood* 123,3855-3863, (2014); Rubnitz, J. E. et al. *J Clin Oncol* 28, 955-959, (2010)). For example, cytokines including IL-2, IL-12, TNF-α, and IL-1 can induce NK cells to produce cytokines. IFN-α and IL-2 are strong inducers of NK cell cytotoxic activity (G. Trinichieri et al., *Journal of Experimental Medicine* 160:1147-1169, 1984; G. Trinichieri and D. Santoli, *Journal of Experimental Medicine* 147: 1314-1333, 1977). The presence of IL-2 both stimulates and expands NK cells (K. Oshimi, *International Journal of Hematology* 63:279-290, 1996). IL-12 has been shown to induce cytokine production from T and NK cells, and augment NK cell-mediated cytotoxicity (M. Kobayashi et al., *Journal of Experimental Medicine* 170:827-846, 1989).

NK cells are involved in both the resistance to and control of cancer spread. Since the advent of the cancer immune surveillance concept, the adoptive transfer of immune cells, particularly T cells and natural killer (NK) cells, has emerged as a targeted method of harnessing the immune system against cancer (Kroemer, G., Senovilla, L., Galluzzi, L., Andre, F. & Zitvogel, L. Natural and therapy-induced immunosurveillance in breast cancer. *Nat Med* 21, 1128-1138, (2015)). NK cells have garnered immense attention as a promising immunotherapeutic agent for treating cancers. NK cells are critical to the body's first line of defense against cancer due to their natural cytotoxicity against malignant cells (Srivastava, S., et al., *Cytotherapy* 10, 775-783; 2008).

NK cells have been expanded from multiple sources, including peripheral blood and umbilical cord blood (CB) ((Denman, C. J. et al. Membrane-bound IL-21 promotes sustained ex vivo proliferation of human natural killer cells, *PLoS One* 7, e30264 (2012); Knorr, D. A. et al. Clinical-scale derivation of natural killer cells from human pluripotent stem cells for cancer therapy. *Stem Cells TranslMed* 2, 274-283, (2013); Shah, N. et al. Antigen presenting cell-mediated expansion of human umbilical cord blood yields log-scale expansion of natural killer cells with anti-myeloma activity. *PLoS One* 8, e76781, (2013); Woll, P. S. et al. Human embryonic stem cells differentiate into a homogeneous population of natural killer cells with potent in vivo antitumor activity. *Blood* 113, 6094-6101, (2009)). Ex vivo NK cell expansion methods have been developed using cytokines in combination with artificial antigen-presenting cells (aAPCs) as feeder cells ((Denman, C. J. et al. *PLoS One* 7, e30264, (2012); Berg, M. et al. *Cytotherapy* 11, 341-355, (2009); Gong, W. et al. *Tissue Antigens* 76, 467-475, (2010); :hang, H. et al., *J Immunother* 34, 187-195, (2011)).

Immune Modulating Molecules

In certain embodiments, one or more immune modulating compounds can be administered as part of the treatment plan. The immune-modulating molecules comprise, but are not limited to cytokines, lymphokines, NK cell stimulating factors, T cell co-stimulatory ligands, etc. An immune-modulating molecule positively and/or negatively influences the humoral and/or cellular immune system, particularly its cellular and/or non-cellular components, its functions, and/ or its interactions with other physiological systems. The immune-modulating molecule may be selected from the group comprising cytokines, chemokines, macrophage migration inhibitory factor (MIF; as described, inter alia, in Bernhagen (1998), *Mol Med* 76(3-4); 151-61 or Metz (1997), *Adv Immunol* 66, 197-223), T-cell receptors or soluble MEW molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Cytokines of the invention are defined by any factor produced by cells that affect other cells and are responsible for any of a number of multiple effects of cellular immunity. Examples of cytokines include but are not limited to the IL-2 family, interferon (IFN), IL-7, IL-10, IL-12, IL-15, IL-18, IL-1, IL-17, TGF and TNF cytokine families, and to IL-1 through IL-35, IFN-α, IFN-β, IFNγ, TGF-β, TNF-α, and TNFβ.

Chemokines, similar to cytokines, are defined as any chemical factor or molecule which when exposed to other cells are responsible for any of a number of multiple effects of cellular immunity. Suitable chemokines may include but are not limited to the CXC, CC, C, and CX3C chemokine families and to CCL-1 through CCL-28, CXC-1 through CXC-17, XCL-1, XCL-2, CX3CL1, MIP-1b, IL-8, MCP-1, and Rantes.

Growth factors include any molecules which when exposed to a particular cell induce proliferation and/or differentiation of the affected cell. Growth factors include proteins and chemical molecules, some of which include: stem cell factors, GM-CSF, G-CSF, human growth factor and stem cell growth factor. Additional growth factors may also be suitable for uses described herein.

Also of interest are enzymes present in the lytic package that NK cells, cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin O and pneumolysin facilitate granzyme B-dependent apoptosis (Browne et al., *Mol. Cell Biol.* 19:8604, 1999).

Pharmaceutical Therapeutics

In one aspect, the pharmaceutical compositions are administered systemically, for example, formulated in a pharmaceutically-acceptable buffer such as physiological saline. Preferable routes of administration include, for example, instillation into the bladder, subcutaneous, intravenous, intraperitoneal, intramuscular, intratumoral or intradermal injections that provide continuous, sustained or effective levels of the composition in the patient. Treatment of human patients or other animals is carried out using a therapeutically effective amount of a therapeutic identified herein in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of the neoplasia. Generally, amounts will be in the range of those used for other agents used in the treatment of other diseases associated with neoplasia or infectious diseases, although in certain instances lower amounts will be needed because of the increased specificity of the compound. A compound is administered at a dosage that enhances an immune response of a subject, or that reduces the proliferation, survival, or invasiveness of a neoplastic or, infected cell as determined by a method known to one skilled in the art.

Formulation of Pharmaceutical Compositions

The administration of compositions embodied herein, is by any suitable means that results in a concentration of the therapeutic that, combined with other components, is effective in ameliorating, reducing, or stabilizing said neoplasia or infectious disease. The composition may be provided in a dosage form that is suitable for parenteral (e.g., subcutaneous, intravenous, intramuscular, intravesicular, intratumoral or intraperitoneal) administration route. For example, the pharmaceutical compositions are formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts are initially determined by extrapolating from the amount of compound used in mice or non-human primates, as a skilled artisan recognizes it is routine in the art to modify the dosage for humans compared to animal models. For example, the dosage may vary from between about 1 μg compound/kg body weight to about 5000 mg compound/kg body weight; or from about 5 mg/kg body weight to about 4,000 mg/kg body weight or from about 10 mg/kg body weight to about 3,000 mg/kg body weight; or from about 50 mg/kg body weight to about 2000 mg/kg body weight; or from about 100 mg/kg body weight to about 1000 mg/kg body weight; or from about 150 mg/kg body weight to about 500 mg/kg body weight. For example, the dose is about 1, 5, 10, 25, 50, 75, 100, 150, 200, 250, 300, 350, 400, 450, 500, 550, 600, 650, 700, 750, 800, 850, 900, 950, 1,000, 1,050, 1,100, 1,150, 1,200, 1,250, 1,300, 1,350, 1,400, 1,450, 1,500, 1,600, 1,700, 1,800, 1,900, 2,000, 2,500, 3,000, 3,500, 4,000, 4,500, or 5,000 mg/kg body weight. Alternatively, doses are in the range of about 5 mg compound/Kg body weight to about 20 mg compound/kg body weight. In another example, the doses are about 8, 10, 12, 14, 16 or 18 mg/kg body weight. In embodiments whereby the N-803 is administered to a patient as part of the therapy, the fusion protein complex is administered at 0.5 mg/kg-about 10 mg/kg (e.g., 0.5, 1, 3, 5, 10 mg/kg). Of course, this dosage amount may be adjusted upward or downward, as is routinely done in such treatment protocols, depending on the results of the initial clinical trials and the needs of a particular patient.

Pharmaceutical compositions are formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

The pharmaceutical compositions embodied herein are administered parenterally by injection, infusion or implantation (subcutaneous, intravenous, intramuscular, intratumoral, intravesicular, intraperitoneal) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions comprising N-803 protein complex for parenteral use are provided in unit dosage forms (e.g., in single-dose ampoules). Alternatively, the composition is provided in vials containing several doses and in which a suitable preservative may be added (see below). The composition is in the form of a solution, a suspension, an emulsion, an infusion device, or a delivery device for implantation, or is presented as a dry powder to be reconstituted with water or another suitable vehicle before use. Apart from the active agent that reduces or ameliorates a neoplasia or infectious disease, the composition includes suitable parenterally acceptable carriers and/or excipients. The active therapeutic agent(s) may be incorporated into microspheres, microcapsules, nanoparticles, liposomes for controlled release. Furthermore, the composition may include suspending, solubilizing, stabilizing, pH-adjusting agents, tonicity adjusting agents, and/or dispersing, agents.

As indicated above, the pharmaceutical compositions may be in a form suitable for sterile injection. To prepare such a composition, the suitable active therapeutic(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol.

The present invention provides methods of treating immunosuppression, neoplasia or infectious diseases or symptoms thereof which comprise administering a therapeutically effective amount of a pharmaceutical composition. Thus, one embodiment is a method of treating a subject suffering from or susceptible to a neoplasia or infectious disease or symptom thereof. The method includes the step of administering to the mammal a therapeutic amount of the compositions embodied herein, in a dose sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a neoplasia, infectious disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The fusion protein complexes of the invention may be used in the treatment of any other disorders in which an increase in an immune response is desired.

The invention also provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with neoplasia in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In some cases, a second level of Marker in the subject is determined at a time point later than the determination of the first level, and the two levels are compared to monitor the course of disease or the efficacy of the therapy. In certain aspects, a pre-treatment level of Marker in the subject is determined prior to beginning treatment according to this invention; this pre-treatment level of Marker can then be compared to the level of Marker in the subject after the treatment commences, to determine the efficacy of the treatment.

Combination Therapies

As described above, the N-803 is administered in combination with an anti-neoplasia or anti-inflammatory therapeutic such as an antibody, e.g., a tumor-specific antibody or an immune-checkpoint inhibitor. The antibody and N-803 may be administered simultaneously or sequentially. In some embodiments, the antibody treatment is an established therapy for the disease indication and addition of N-803 treatment to the antibody regimen improves the therapeutic benefit to the patients. Such improvement could be measured as increased responses on a per patient basis or increased responses in the patient population. Combination therapy could also provide improved responses at lower or less frequent doses of antibody resulting in a better tolerated treatment regimen. As indicated, the combined therapy of N-803 and an antibody could provide enhances clinical activity through various mechanisms, including augmented ADCC, ADCP, and/or NK cell, T-cell, neutrophil or monocytic cell levels or immune responses.

If desired, N-803 is administered in combination with any conventional therapy, including but not limited to, surgery, radiation therapy, chemotherapy, protein-based therapy or biological therapy. Chemotherapeutic drugs include alkylating agents (e.g., platinum-based drugs, tetrazines, aziridines, nitrosoureas, nitrogen mustards), anti-metabolites (e.g., antifolates, fluoropyrimidines, deoxynucleoside analogues, thiopurines), anti-microtubule agents (e.g., vinca alkaloids, taxanes), topoisomerase inhibitors (e.g., topoisomerase I and II inhibitors), cytotoxic antibiotics (e.g., anthracyclines) and immunomodulatory drugs (e.g., thalidomide and analogs).

In certain embodiments, a composition for eradicating a retrovirus in vitro or in vivo, comprises a therapeutically effective amount of: IL-15:IL-15Rα. In addition, one or more agents which alleviate any other symptoms that may be associated with the virus infection, e.g. fever, chills, headaches, secondary infections, can be administered in concert with, or as part of the pharmaceutical composition or at separate times. These agents comprise, without limitation, an anti-pyretic agent, anti-inflammatory agent, chemotherapeutic agent, or combinations thereof.

In certain embodiments, the anti-viral agent comprises therapeutically effective amounts of: antibodies, aptamers, adjuvants, anti-sense oligonucleotides, chemokines, cytokines, immune stimulating agents, immune modulating molecules, B-cell modulators, T-cell modulators, NK cell modulators, antigen presenting cell modulators, enzymes, siRNA's, interferon, ribavirin, ribozymes, protease inhibitors, anti-sense oligonucleotides, helicase inhibitors, polymerase inhibitors, helicase inhibitors, neuraminidase inhibitors, nucleoside reverse transcriptase inhibitors, non-nucleoside reverse transcriptase inhibitors, purine nucleosides, chemokine receptor antagonists, interleukins, vaccines or combinations thereof.

The immune-modulating molecules comprise, but are not limited to cytokines, lymphokines, T cell co-stimulatory ligands, etc. An immune-modulating molecule positively and/or negatively influences the humoral and/or cellular immune system, particularly its cellular and/or non-cellular components, its functions, and/or its interactions with other physiological systems. The immune-modulating molecule may be selected from the group comprising cytokines, chemokines, macrophage migration inhibitory factor (MIF; as described, inter alia, in Bernhagen (1998), *Mol Med* 76(3-4); 151-61 or Metz (1997), *Adv Immunol* 66, 197-223), T-cell receptors or soluble MHC molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2):167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to, (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Also of interest are enzymes present in the lytic package that cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin O and pneumolysin facilitate granzyme B-dependent apoptosis (Browne et al., *Mol. Cell Biol.* 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Exemplary is thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

In certain embodiments, the antiviral agent comprises natural or recombinant interferon-alpha (IFNα), interferon-beta (IFNβ), interferon-gamma (IFNγ), interferon tau (IFNτ), interferon omega (IFNω), or combinations thereof. In some embodiments, the interferon is IFNγ. Any of these interferons can be stabilized or otherwise modified to improve the tolerance and biological stability or other biological properties. One common modification is pegylation (modification with polyethylene glycol).

Kits or Pharmaceutical Systems

Any of the pharmaceutical compositions of the invention can be formulated for use in the preparation of a medicament, and particular uses are indicated below in the context of treatment, e.g., the treatment of a subject having an HIV infection or at risk for contracting and HIV infection.

Pharmaceutical compositions comprising N-803 may be assembled into kits or pharmaceutical systems for use in modulating immune activity or number of circulating immune cells or treating a neoplasia or autoimmune or inflammatory disease. Kits or pharmaceutical systems according to this aspect of the invention comprise a carrier means, such as a box, carton, tube, having in close confinement therein one or more container means, such as vials, tubes, ampoules, bottles, syringes, or bags. The kits or pharmaceutical systems of the invention may also comprise associated instructions for using N-803.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Interleukin-15 Super-Agonist (N-803) Treatment of Progressive Multifocal Leukoencephalopathy (PML) and JC Polyomavirus (ICV) in a Post-Allogeneic Hematopoietic Stem Cell Transplant Patient (HCT)

Progressive multifocal leukoencephalopathy (PML) is a rare demyelinating disease of the central nervous system (CNS) caused by reactivation of the John Cunningham polyomavirus (JCV). JCV is common, and while 50 to 70% of adults in the general population are seropositive, most will remain asymptomatic. Two varieties of JCV have been identified: the archetypal variant excreted in the urine of asymptomatic carriers, and the prototypical variant associated with PML. The mechanisms by which the immune system controls latent JCV infection have not been elucidated, but both the humoral and cellular immune systems seem to play a role. In the setting of immunosuppression the virus is reactivated, and ultimately infects the oligodendrocytes in the CNS resulting in demyelination. The disease usually presents with focal neurologic deficits, most commonly weakness and motor disturbances. Following a course of progressive neurologic decline, PML is generally rapidly fatal.

PML affects severally immunocompromised patients. Historically associated with HIV/AIDS, it also occurs in patients with hematologic malignancies, autoimmune conditions, and in patients taking monoclonal antibodies such as rituximab and natalizumab. With increased use of hematopoietic stem cell transplant (HCT) and improved survival among this population, PML is now recognized as a fatal complication of allogeneic HCT.

There is no effective antiviral treatment for JCV or PML, but immune reconstitution is essential. In the post-transplant setting, the risk of developing PML does not appear to have an endpoint, and time to development of symptoms can range from weeks to decades. In one study, the median time to development of symptoms among stem cell transplant recipients was 11 months, with a median survival of 19.5 months.

Methods

A 27-year-old HIV-negative male with no significant past medical history was diagnosed with T-cell acute lymphoblastic leukemia in January 2016. The patient was treated according to the CALGB 10403 protocol, and CSF cytology was negative at diagnosis and remained negative throughout therapy. He eventually received a 10/10 matched-unrelated donor allogeneic HCT in May 2016. The patient achieved MRD negativity with complete donor engraftment. There was minimal GVHD, and all immunosuppression (tacrolimus and mycophenolate mofetil) was tapered off by February 2017. CD4 count at this time was 458. The patient was free of any neurologic deficits and was able to return to work full time.

On Jul. 14, 2017, 460 days post-transplant, the patient presented with left shoulder pain associated with left arm heaviness. There was no history of injuries or trauma. Physical exam was remarkable for asymmetric left shoulder fullness, but no weakness or neurologic deficits. A cervical spine MM was unremarkable, and CSF analysis showed no evidence of leukemia. Ten days later, he reported new weakness in the left lower and upper extremities, with loss of fine motor skills in the left hand, but no numbness or sensory deficits. Physical examination primarily revealed proximal muscle weakness: the patient was unable to shrug his left shoulder, raise his left arm up to shoulder level, perform finger opposition, or flex his left lower extremity at the hip. Deep tendon reflexes in the left upper and lower extremities were also diminished. A short course of prednisone (2 mg/kg×7 days) was administered, with no improvement.

Over the next week the patient's weakness progressed to paralysis, and he was no longer able to ambulate, requiring a wheelchair. On examination he was not able raise his left upper or lower extremities against gravity. A brain MRI was obtained which showed a posterior right frontal subcortical white matter lesion, hyperintense on T2/FLAIR without enhancement or diffuse restriction, concerning for PML. A repeat lumbar puncture was performed, and qualitative PCR, performed at Barnes-Jewish Hospital was positive for JCV, confirming the diagnosis. A quantitative DNA PCR for JCV was not performed at the time. Mefloquine 250 mg daily and mirtazapine 30 mg daily were initiated on Aug. 7, 2017. Due to lack of improvement and progression of weakness after 14 days, N-803, an IL-15 super agonist, (6 µg/kg on days 1, 8, 15 and 22 of a 28-day cycle) was added under compassionate use (Single-Patient IND #136501) from the FDA on Aug. 21, 2017.

Cryopreserved peripheral blood mononuclear cells were thawed, washed, and resuspended in staining buffer (PBS supplemented with 0.5% bovine serum albumin and 2 mM EDTA). Cells were incubated for 30 min at room temperature with pre-titrated saturating dilutions of the following fluorochrome-labeled monoclonal antibodies (BD Biosciences, San Jose, CA or Biolegend, San Diego, CA; clone designated in parenthesis): CD3 (UCHT1), CD4 (SK3), CD8 (SK1), CD14 (MφP9), CD19 (HIB19), CD25 (M-A251), CD28 (CD28.2), CD38 (HIT2), CD45 (2D1), CD45RA (HI100), CD56 (NCAM16.2), CD69 (FN50), CD123 (7G3), CD152 (BNI3), CD183 (1C6), CD193 (5E8), CD194 (L291H4), CD196 (G034), CD197 (150503), CD223 (T47-530), CD279 (EH12.2H7), CD303 (AC144), CD366 (F38-2E2), granzyme B (MHGB05), HLA-DR (G46-6), Foxp3 (236A/E7), KI67 (B56), and perforin (δG9). Dead cells were excluded by staining with 2 µg/ml 7-aminoactinomycin D (Molecular Probes, Eugene, OR) or a LIVE/DEAD fixable blue dead cell stain kit (Thermo Fisher Scientific, Waltham, MA). Intracellular staining was performed with a Foxp3 transcription factor staining buffer set (Thermo Fisher Scientific). Appropriate fluorescence minus one and isotype-matched negative controls were used to assess background fluorescence intensity and set gates for negative populations. Samples were analyzed on a Gallios (Beckman Coulter, Brea, CA) or ZE5 (Bio-Rad, Hercules, CA) flow cytometer and data were analyzed using FlowJo software (TreeStar, Ashland, OR).

Results

Figure 1B:
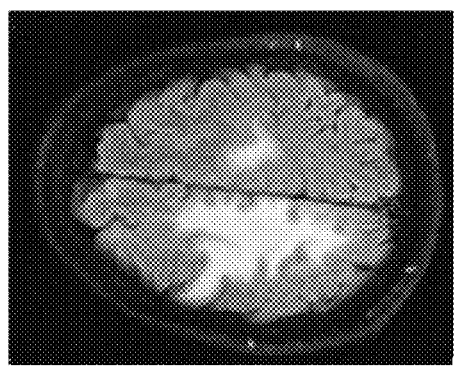
Figure 1A:
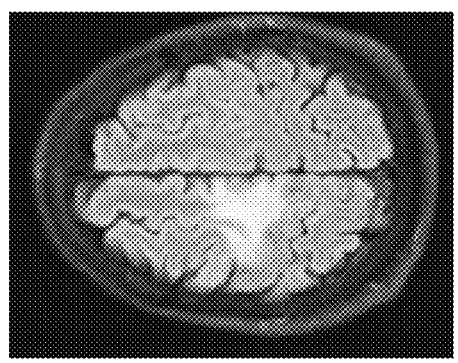

A repeat brain MRI was obtained after two cycles on Oct. 16, 2017 which showed worsening extent of the FLAIR abnormality (FIGS. 1A-1C). However, the patient felt that his strength was improving which was confirmed on physical examination, and treatment was continued. Subsequent brain MRIs demonstrated marked improvement in the T2/FLAIR white matter lesions and the most recent brain MRI, eight months after initiation of N-803, continues to demonstrate response. Qualitative CSF JCV PCR at our institution has remained negative since December 2017. CSF specimens were sent to the NIH for ultrasensitive quantitative JCV PCR, and the DNA copy number performed at the NIH decreased from 31 copies/ml in December 2017, to 16 copies/ml in February 2018, and 11 copies/ml in April 2018. Sequencing of the JCV performed at the NIH demonstrated the prototypical variant. N-803 was stopped after eight total cycles and the patient continued to take mefloquine and mirtazapine. His neurologic deficits continue to improve, and he is now able to ambulate with a cane.

Peripheral blood cell subsets were measured by flow cytometry. While the absolute number of circulating T and B cells decreased during N-803 treatment, a >3.5-fold increase in the number of circulating NK cells was observed (FIG. 2A). Comprehensive phenotyping of peripheral blood T cell subsets by flow cytometry revealed little to no changes within the $CD3^+CD4^+$ T cell subsets (FIGS. 2B-2F). In contrast, there was a decrease in the relative percentage of naïve $CD3^+CD8^+$ T cells with a concomitant increase in effector memory (EM) and effector memory RA (EMRA) cells during N-803 treatment. This shift in the $CD3^+CD8^+$ T cell population towards an effector phenotype was accompanied by an increase in the number of CXCR3 expressing cells as well as evidence of temporary cell activation as determined by increased expression of CD38, HLA-DR, perforin (Pfn), granzyme B (GzmB), and the proliferation marker Ki-67 (FIGS. 2B-2F).

Discussion

This is one of the first in vivo in-human cases demonstrating that N-803 enhances the clearance and resolution of a viral illness. A preclinical study performed in monkeys showed that N-803 lead to suppressed replication of simian immunodeficiency virus, an HIV-like virus which results in an AIDS-like disease in non-human primates. Preliminary data from an ongoing phase I trial of N-803 in $HIV^+$ patients demonstrated that treatment with N-803 resulted in increased numbers of $CD4^+$ and $CD8^+$ T cells, increased NK cells, as well as increased HIV transcription. A recently reported in-human case of recurrent cytomegalovirus reactivation in a post-allogeneic HCT patient demonstrated that treatment with N-803 was associated with temporary viral clearance. Of note previous in-human studies suggest that N-803 may enhance the clearance of relapsed refractory AML in vivo, without increasing rates of immunosuppression-requiring GVHD. Thus, this work provides evidence that N-803 may not only have important therapeutic benefit in patients with cancer but also in immunocompromised patients with life-threatening viral infections.

IL-15 and N-803 induce both expansion and activation of NK and central memory CD8 T cells. While the present study demonstrated a decrease in absolute number of circulating T and B cells during N-803 treatment, there was an increase in EM and EMRA cells. Also observed was an increase in circulating NK cells. These findings are consistent with previously reported data.

PML is a progressive, typically fatal disease affecting severely immunocompromised patients. There is no effective prophylaxis or anti-viral treatment against the causative JCV, and immune reconstitution is necessary for recovery. In patients with HIV/AIDS, initiation of HAART has been associated with improved outcomes. In natalizumab-associated PML, discontinuation of the drug and initiation of plasma exchange are effective. However, no such standard approach exists in post-transplant PML. One generally accepted approach is discontinuation of immunosuppression, which raises the risk of GVHD. Of note, the patient was off all immunosuppressive therapy for 5 months prior to the development of symptoms. Other treatment strategies have been proposed, but evidence remains limited to case reports. One such approach includes the regimen of mirtazapine and mefloquine. A randomized controlled trial of mefloquine for treatment of PML was opened, however it was terminated early after a pre-planned interim analysis suggested no therapeutic benefit would be found. Due to flaws in the study design, it is believed that the effect of mefloquine in HIV-negative patients was not adequately assessed, and it is still accepted as a therapeutic option in PML in this setting. While no randomized trials exist for mirtazapine therapy, multiple case reports have been published showing potential benefit.

More novel therapeutic approaches have included immunotherapy, and case reports supporting the use of IL-2 and IL-7 have been published. Interleukin-15 is a cytokine that is critical for the proliferation and activation of natural killer cells and $CD8^+$ memory T cells. Lymphopenia is the main risk factor for PML, and the lesions typically lack a lymphocytic infiltrate. Upon immune restoration, $CD8^+$ T cell-predominant lymphocytic infiltrates develop, often corresponding with transiently worsening symptoms, MRI findings or both. This process, called immune reconstitution inflammatory syndrome (IRIS), is perhaps consistent with our patient's observed MRI findings after two cycles of N-803. Brain biopsies/autopsy samples from $HIV^+$ and $HIV-$ patients with PML demonstrated that recruitment of CD8+ T cells is associated with control of the JCV infection.

Here, it is reported that a case of post-allogeneic HCT PML was successfully treated with N-803, a novel recombinant human IL-15 super-agonist developed by NantCell, LLC (Culver City CA). N-803 contains a mutant form of IL-15 (N72D), in complex with the soluble domain of the IL-15 receptor (IL-15Rα), resulting in a prolonged serum half-life and increased biologic activity compared with wild-type IL-15.

The patient received 8 cycles of N-803. Nine months after the diagnosis of PML was made, the patient continues to show evidence of recovery by CSF analysis, imaging and on physical examination. Moreover, he has had no evidence of GVHD, remains completely engrafted and in remission. Thus, N-803 represents a therapeutic option for treatment of PML in post-allogeneic HCT patients and further prospective studies are to be conducted.

Example 2: Phase I Study of N-803 in HIV Infected Patients to Clear Latent HIV Reservoirs The rationale for the treatment of patients infected with human immunodeficiency (HIV) with IL-15:IL-15Rα complex (N-803) is several fold. It induces virus from latency; activates and induces proliferation of NK cells and $CD8^+$ T cells (CTLs), HIV-specific CTLs infiltrate B cell follicular lymphoid follicles; the N-803 concentrates in the lymph nodes and has a long half-life, e.g. about 3-5 days.

Figure 3:
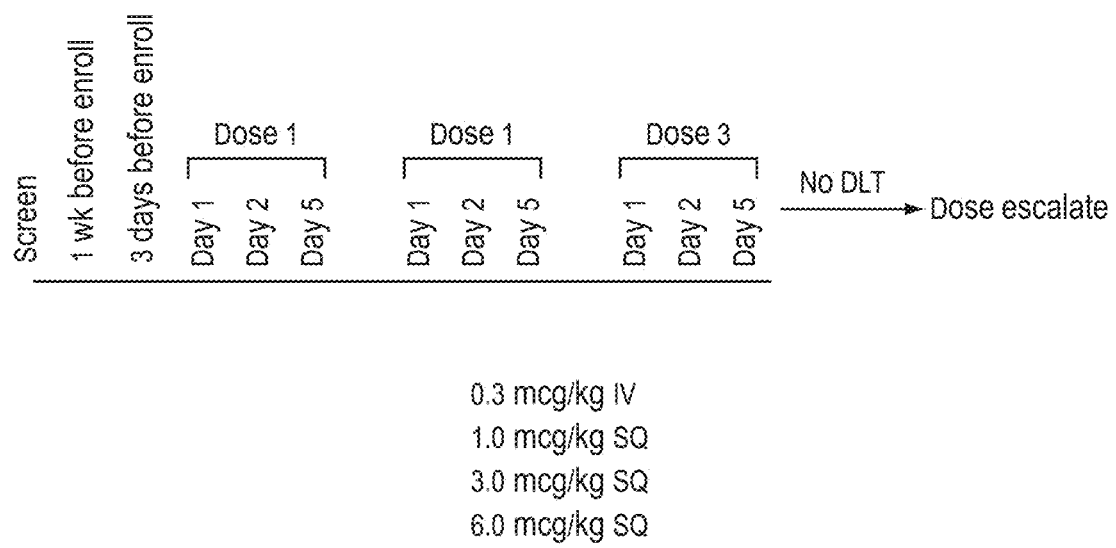
FIG. 3 is a schematic representation of the phase I dose escalation study in HIV infected subjects. The protocol initially started with administration of 0.3 mcg/kg intravenously then switched to subcutaneous (SQ) administration. Doses were administered at days 1, 2 and 5 with an escalation of per dose: Dose 1 was 1.0 mcg/kg SQ, dose 2 was 3.0 mcg/kg SQ; dose 3 was 6.0 mcg/kg SQ. The doses would escalate if no dose-limiting toxicity (DLT) was observed.

FIG. 3 is a schematic representation of the phase I dose escalation study in HIV infected subjects. The protocol initially started with administration of 0.3 mcg/kg intravenously then switched to subcutaneous (SQ) administration. Doses were administered at days 1, 2 and 5 with an escalation of per dose: Dose 1 was 1.0 mcg/kg SQ, dose 2 was 3.0 mcg/kg SQ; dose 3 was 6.0 mcg/kg SQ. The doses would escalate if no dose-limiting toxicity (DLT) was observed.

FIG. 4 is a table depicting the demographic characteristics of the patients enrolled in the study. The average age being 43 years old, average CD4+ T cell count of 821, the average number of years that the subjects were $HIV^+$ was 12 years and the average number of years that the patients were on anti-retroviral therapy was 9.

Figure 5:
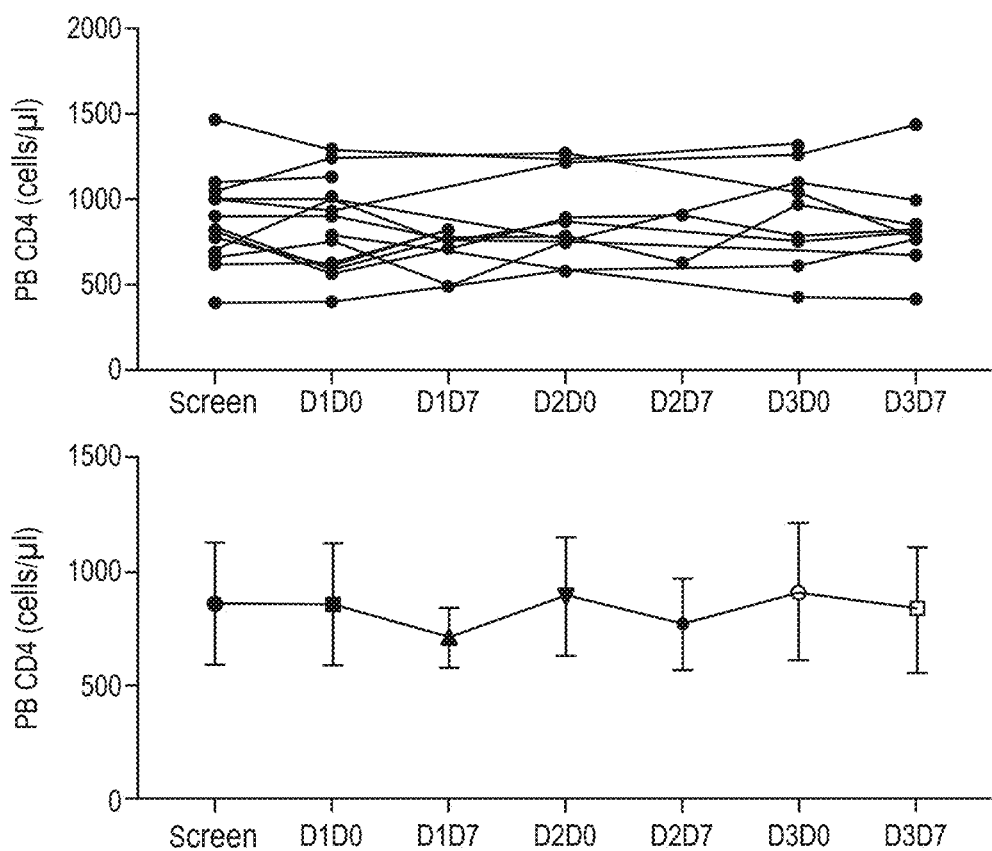
FIG. 5 is a graph showing that the peripheral blood CD4 T cell count did not change over the period of administration of the doses.

FIG. 5 is a graph showing that the peripheral blood CD4 T cell count did not change over the period of administration of the doses.

Figure 6:
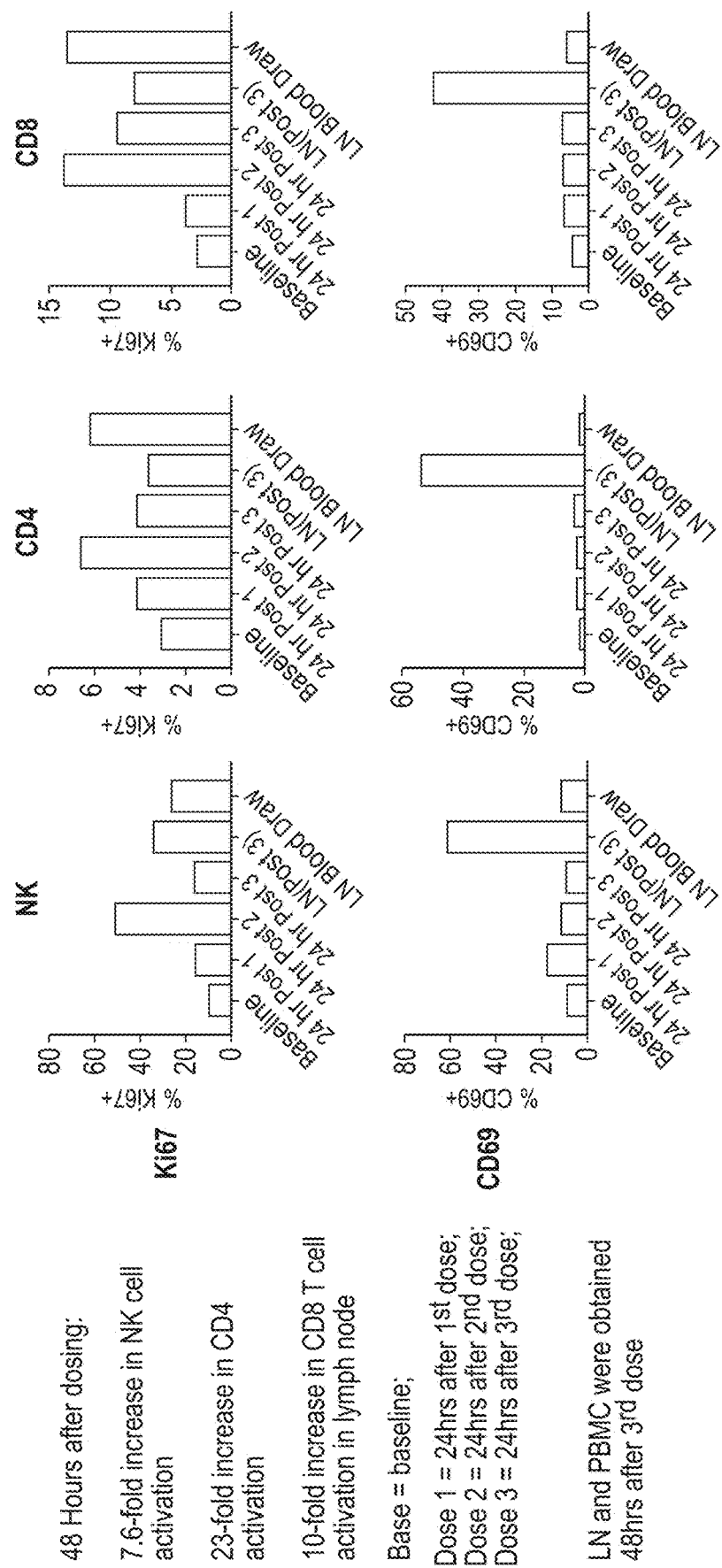
FIG. 6 is a series of graphs demonstrating that the N-803 induces proliferation (Ki67) and activation (CD69) of CD4, CD8, and NK cells after each dose of N-803. 48 hours after dosing: a 7.6-fold increase in NK cell activation was observed; a 23-fold increase in CD4 activation and 10-fold increase in CD8 T cell activation in lymph node. The lymph node (LN) and peripheral blood mononuclear cells (PBMC) were obtained 48 hrs. after 3rd dose.

FIG. 6 demonstrates that the N-803 induces proliferation (Ki67) and activation (CD69) of CD4, CD8, and NK cells after each dose of N-803. 48 hours after dosing: a 7.6-fold increase in NK cell activation was observed; a 23-fold increase in CD4 activation and 10-fold increase in CD8 T cell activation in lymph node. The lymph node (LN) and peripheral blood mononuclear cells (PBMC) were obtained 48 hrs. after 3rd dose.

Figure 7:
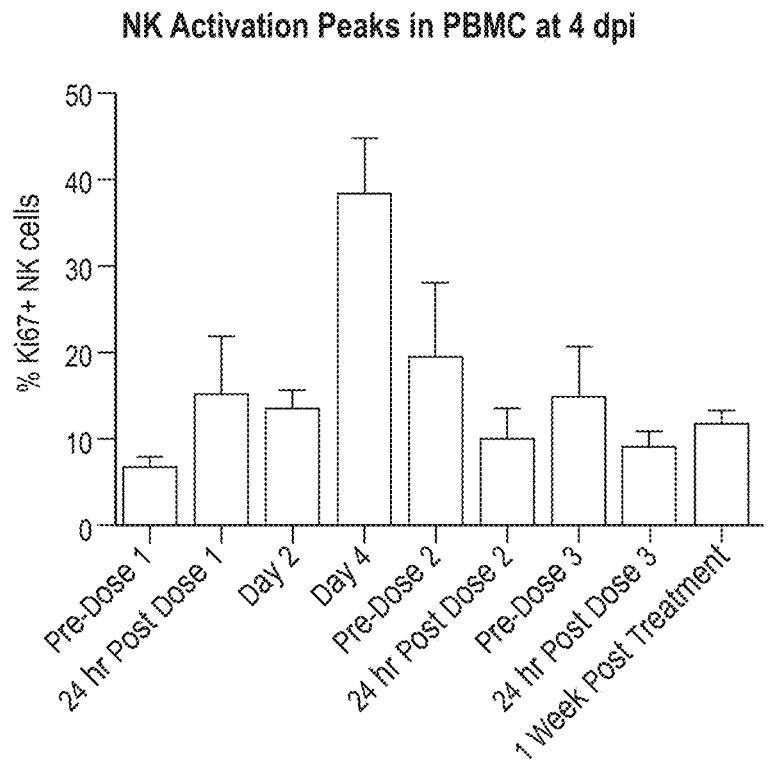
FIG. 7 is a graph demonstrating that the NK cell activation peaks at 4 days post inoculation.

FIG. 7 is are results from clinical data demonstrating that the NK cell activation peaks at 4 days post inoculation.

Figure 8:
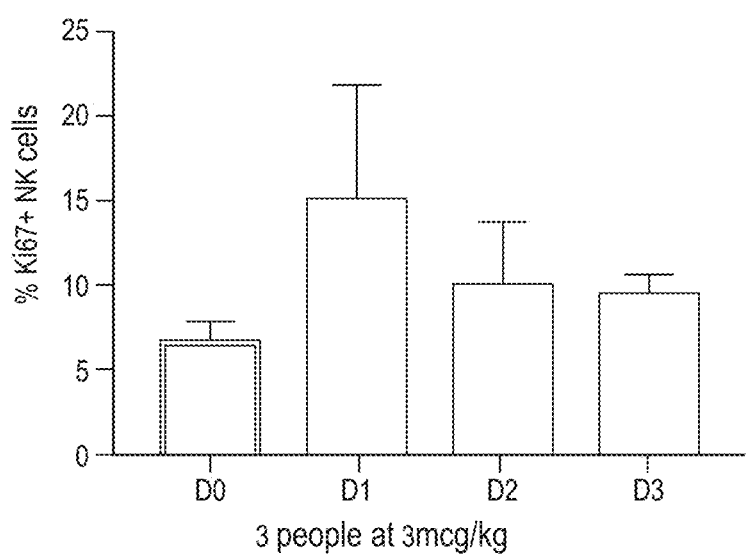
FIG. 8 is a graph demonstrating that there is a decrease in NK cell activation with too frequent dosing.

FIG. 8 are results from clinical data demonstrating that there is a decrease in NK cell activation with too frequent dosing.

FIG. 9 shows the infiltration of CD20 and CD8 positive cells in a patient after administration of 6 mcg/kg N-803.

FIGS. 10A and 10B demonstrate that N-803 induces homing of NK cells to lymph nodes where latently HIV-infected cells reside. The NK cells can potentially kill HIV-infected cells. FIG. 10A is a CD56 staining of the lymph nodes before N-803 administration. FIG. 10B shows the infiltration of CD56 positive cell into the lymph nodes after a $3^{rd}$ dose of N-803 (3.0 mcg/kg subcutaneously).

The detection of HIV was conducted by the an assay termed herein as the EDITS (Env Detection by Induced Transcript Sequencing) assay based on the detection of env transcription. Biswajit Das et al., *Proceedings of the National Academy of Sciences* August 2018, 115 (33) E7795-E7804; DOI: 10.1073/pnas.1803468115).

Figure 11:
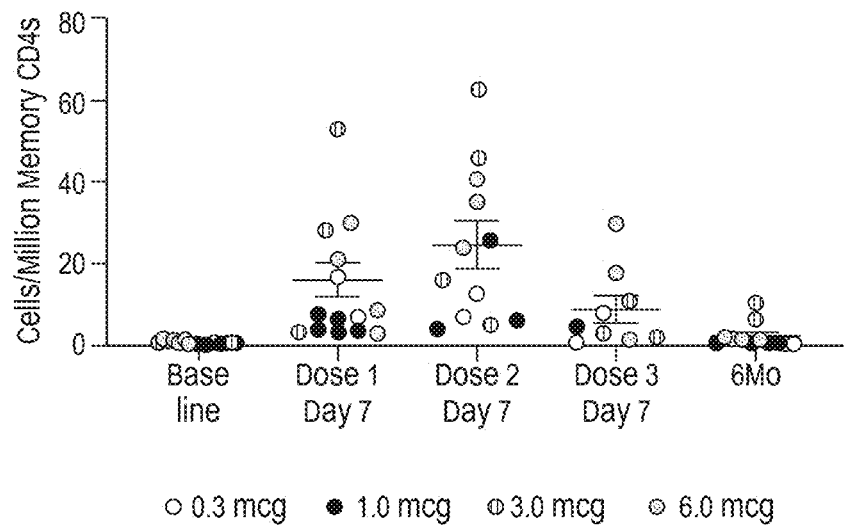
FIG. 11 is a graph demonstrating that N-803 induces HIV transcription in lymphocytes.

FIG. 11 shows that N-803 induces HIV transcription in lymphocytes without stimulation. This was a direct measure of the impact of N-803 on virus transcription of dose 1, dose 2 and dose 3 at day 7 post-administration.

Figure 12:
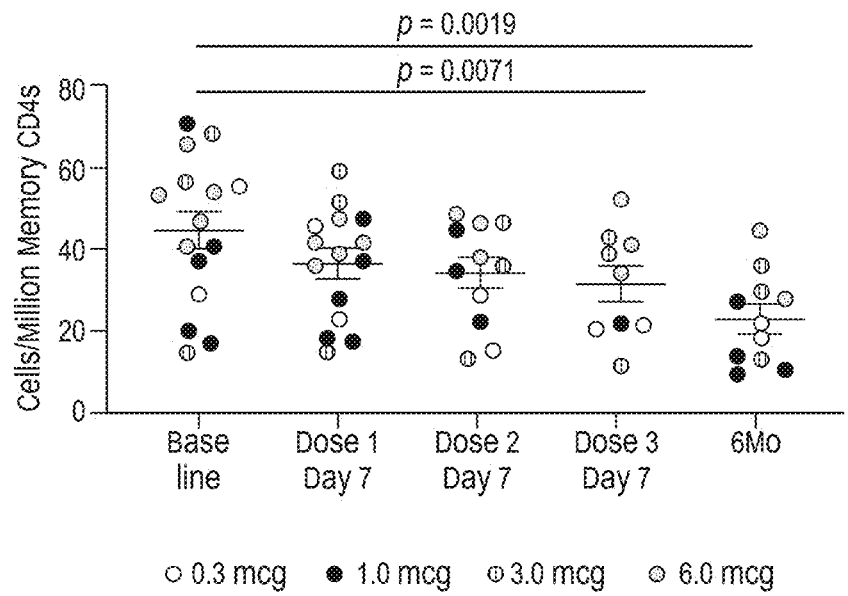
FIG. 12 is a graph demonstrating that N-803 decreased detectable HIV reservoir in lymphocytes.

FIG. 12 shows that N-803 decreased the detectable HIV reservoir in lymphocytes. This was a measure of the overall size of the inducible reservoir after stimulation with ConA.

The clinical results from the studies conducted herein demonstrate that patients tolerated doses of N-803 up to 6 mcg/kg; T cells and NK cells were activated and proliferated; there was evidence for virus transcription; the reservoir of HIV in peripheral blood mononuclear cells (PBMCs) was reduced; no evidence of IL-15 antibodies and there were no side effects related to cytokines.

Equivalents

Those skilled in the art will recognize, or be able to ascertain using no more than routine experimentation, many equivalents to the specific embodiments of the invention described herein. Such equivalents are intended to be encompassed by the following claims.

What is claimed:

1. A kit for use in treating human immunodeficiency virus (HIV) latent infection in a subject in need thereof, the kit comprising:
   a. isolated immune effector cells, stem cells, or a combination thereof, wherein the immune effector cells are selected from the group consisting of natural killer cells (NK) cytolytic CD8$^+$T cells (CTLs), CD4$^+$T helper cells ($T_H$), effector memory ($T_{EM}$) T cells (CD45RA$^-$/CCR7$^-$), effector memory RA ($T_{EMRA}$) T cells (CD45RA$^+$/CCR7$^-$), and combinations thereof;
   b. a composition comprising from about 1 mcg/kg up to 6.0 mcg/kg of an IL-15:IL-15Rα complex wherein the IL-15:IL-15Rα complex is an IL-15N72D:IL-15RαSu/Fc complex comprising a dimeric IL-15RαSu/Fc and two IL-15N72D molecules;
   c. an adjuvant, wherein the adjuvant is a synthetic toll-like receptor-7/8 (TLR7/8) agonist; and
   d. instructions for using the kit.

2. The kit of claim 1, wherein the kit further comprises a carrier selected from the group consisting of a box, carton, and tube.

3. The kit of claim 1, wherein the kit further comprises a container selected from the group consisting of vials, tubes, ampoules, bottles, syringes, and bags.

4. The kit of claim 1 further comprising one or more chemotherapeutic agents, cytokine antagonist, cytokine receptor antagonist, cytokines, adoptive cell therapy, antiviral agents, checkpoint inhibitors, or combinations thereof.

5. The kit of claim 4, wherein the anti-viral agent comprises: a non-nucleoside reverse transcriptase inhibitor (NNRTI) selected from the group consisting of etravirine, efavirenz, nevirapine, rilpivirine, delavirdine, and combinations thereof; a nucleoside reverse transcriptase inhibitor (NRTI) selected from the group consisting of lamivudine, zidovudine, emtricitabine, abacavir, zalcitabine, dideoxycytidine, azidothymidine, tenofovir disoproxil fumarate, didanosine (ddI EC), dideoxyinosine, stavudine, abacavir sulfate, and combinations thereof; a protease inhibitor selected from the group consisting of amprenavir, tipranavir, indinavir, saquinavir mesylate, lopinavir and ritonavir (LPV/RTV), Fosamprenavir Calcium (FOS-APV), ritonavir, darunavir, atazanavir sulfate, nelfinavir mesylate, and combinations thereof; or combinations thereof.

6. The kit of claim 1 further comprising a pharmaceutically acceptable buffer.

7. The kit of claim 6, wherein the buffer is physiological saline.

8. The kit of claim 1, wherein the composition is in a dosage form suitable for parenteral administration.

9. The kit of claim 1, wherein the composition is in the form of a solution, a suspension, an emulsion or is presented as a dry powder to be reconstituted in a parentally acceptable liquid vehicle and/or solvent.

10. The kit of claim 9, wherein the parentally acceptable liquid vehicle and/or solvent is selected from the group consisting of water, 1,3-butanediol, Ringer's solution, isotonic sodium chloride solution and dextrose solution.

11. The kit of claim 10, wherein the water is adjusted to a suitable pH by addition of an appropriate amount of hydrochloric acid, sodium hydroxide or a suitable buffer.

12. The kit of claim 1, wherein the composition is formulated with an excipient, carrier and/or a preservative.

13. The kit of claim 1, wherein the composition is in a unit dosage form.

14. The kit of claim 1, wherein the composition is incorporated into microspheres, microcapsules, nanoparticles, or liposomes.

15. The kit of claim 1, wherein the kit further comprises a histone deacetylase (HDAC) inhibitor.

* * * * *